US012133913B2

(12) United States Patent
Giesing

(10) Patent No.: US 12,133,913 B2
(45) Date of Patent: *Nov. 5, 2024

(54) METHODS OF TREATING OVERACTIVE BLADDER USING TROSPIUM

(71) Applicant: TARIS BIOMEDICAL LLC, Lexington, MA (US)

(72) Inventor: Dennis Giesing, Lee's Summit, MO (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,325

(22) Filed: Aug. 11, 2022

(65) Prior Publication Data

US 2023/0075003 A1 Mar. 9, 2023

Related U.S. Application Data

(63) Continuation of application No. 16/528,032, filed on Jul. 31, 2019, now Pat. No. 11,464,734.

(60) Provisional application No. 62/850,481, filed on May 20, 2019, provisional application No. 62/713,414, filed on Aug. 1, 2018.

(51) Int. Cl.
*A61K 9/00* (2006.01)
*A61K 31/439* (2006.01)
*A61P 13/10* (2006.01)

(52) U.S. Cl.
CPC .......... *A61K 9/0034* (2013.01); *A61K 31/439* (2013.01); *A61P 13/10* (2018.01)

(58) Field of Classification Search
CPC .... A61K 9/0034; A61K 31/439; A61K 31/46; A61P 13/10; A61M 2210/1085
See application file for complete search history.

(56) References Cited

U.S. PATENT DOCUMENTS

| | | |
|---|---|---|
| 5,998,430 A | 12/1999 | Schwantes |
| 7,390,816 B2 | 6/2008 | Aberg |
| 8,343,516 B2 | 1/2013 | Daniel |
| 8,679,094 B2 | 3/2014 | Cima |
| 8,690,840 B2 | 4/2014 | Lee et al. |
| 8,801,694 B2 | 8/2014 | Lee et al. |
| 9,017,312 B2 | 4/2015 | Lee et al. |
| 9,107,816 B2 | 8/2015 | Lee |
| 9,757,546 B2 | 9/2017 | Daniel |
| 10,500,200 B2 | 12/2019 | Giesing |
| 11,464,734 B2 | 10/2022 | Giesing et al. |
| 2006/0154951 A1 | 7/2006 | Wood |
| 2007/0202151 A1 | 8/2007 | Lee et al. |
| 2009/0149833 A1 | 6/2009 | Cima et al. |
| 2010/0331770 A1 | 12/2010 | Lee |
| 2011/0060309 A1 | 3/2011 | Lee et al. |
| 2011/0152839 A1 | 6/2011 | Cima et al. |
| 2012/0191068 A1 | 7/2012 | Himes et al. |
| 2012/0203203 A1 | 8/2012 | Lee |
| 2013/0158675 A1 | 6/2013 | Hutchins, III |
| 2013/0324946 A1 | 12/2013 | Tobias et al. |
| 2014/0276636 A1 | 9/2014 | Lee |
| 2015/0165177 A1 | 6/2015 | Giesing |
| 2015/0165178 A1 | 6/2015 | Giesing |
| 2015/0250717 A1 | 9/2015 | Giesing |
| 2015/0360012 A1 | 12/2015 | Sansone |
| 2016/0008271 A1 | 1/2016 | Lee |
| 2016/0199544 A1 | 7/2016 | Lee |
| 2016/0279399 A1 | 9/2016 | Lee |
| 2016/0310715 A1 | 10/2016 | Lee |
| 2019/0060344 A1 | 2/2019 | Giesing |
| 2020/0060966 A1 | 2/2020 | Giesing |
| 2020/0108057 A1 | 4/2020 | Giesing |

FOREIGN PATENT DOCUMENTS

| | | |
|---|---|---|
| EP | 1632229 A1 | 3/2006 |
| EP | 2719374 A1 | 4/2014 |
| JP | 2007517912 A | 7/2007 |
| JP | 2008517031 A | 5/2008 |
| JP | 2018070660 A | 5/2018 |
| RU | 2435610 C2 | 12/2011 |
| WO | 2004052440 A1 | 6/2004 |
| WO | 2005067890 A2 | 7/2005 |
| WO | 2006045640 A1 | 5/2006 |
| WO | 2006101954 A2 | 9/2006 |
| WO | 2006101954 A3 | 1/2007 |
| WO | 2007027675 A1 | 3/2007 |
| WO | 2008107446 A1 | 9/2008 |
| WO | 2011031855 A2 | 3/2011 |
| WO | 2011031855 A3 | 4/2012 |
| WO | 2014047221 A1 | 3/2014 |

(Continued)

OTHER PUBLICATIONS

Amend, B. et al. (2008, e-pub. Jan. 17, 2008). "Effective Treatment of Neurogenic Detrusor Dysfunction by Combined High-Dosed Antimuscarinics Without Increased Side-Effects," European Urology 53:1021-1028.

Andersson, K.E. et al. (2016). "Chapter 68—Pharmacologic Management of Lower Urinary Tract Storage and Emptying Failure," in Section XIV Urine Transport, Storage, and Emptying 1967-2002. e14, 50 pages.

Birder, L. et al. (Apr. 2013). "Urothelial Signaling," Physiol Rev. 93(2):653-680, 28 pages.

Coyne, K. et al. (2015). "181: An Overactive Bladder Symptom and Quality-of-Life Short Form: Development of the Overactive Bladder Questionaire (OAB-Q) Short Form (SF)," 2 pages.

Daly, D.M. et al. (Jul. 2011), "The Afferent System and Its Role In Lower Urinary Tract Dysfunction," Current Opinion in Urology 21(4):268-274.

De Groat, W.C. et al. (2009). "Afferent Nerve Regulation of Bladder Function in Health and Disease," Handbook Exp Pharmacol. 194:91-138, 45 pages.

(Continued)

Primary Examiner — Sahar Javanmard
(74) Attorney, Agent, or Firm — Morrison & Foerster LLP

(57) ABSTRACT

The present application provides methods of treating overactive bladder and methods of training or retraining bladder, prolonging symptom relief, improving the quality of life and/or neuronal remodeling in an individual having overactive bladder, by administering an effective amount of trospium locally to the bladder of the individual for at least about 24 hours.

20 Claims, 15 Drawing Sheets

(56) References Cited

FOREIGN PATENT DOCUMENTS

| WO | 2014144066 A1 | 9/2014 |
| WO | 2014145638 A1 | 9/2014 |
| WO | 2015026813 A1 | 2/2015 |
| WO | 2014047221 A9 | 5/2015 |
| WO | 2015200752 A1 | 12/2015 |
| WO | 2016172704 A1 | 10/2016 |
| WO | 2017042370 A1 | 3/2017 |
| WO | 2018144738 A1 | 8/2018 |

OTHER PUBLICATIONS

Fröhlich et al. (1998). "Intravesical Application of Trospium Chloride, Oxybutynin and Verapamil for Relaxation of the Urinary Bladder Detrusor Muscle," Arzneim.Forsch/Drug Res. 48(1):486-491.

Grosse, J.O. et al. (Apr. 26, 2009). "Abstract 1590—Release of Trospium Chloride from Expanded PLGA Carriers as Intravescial Delivery," The Journal of Urology 181(4):571, 1 page.

Haferkamp, A. et al. (Oct. 1, 2006). "Intravesical Treatment of Overactive Bladder Syndrome," Der Urologe 45 (10):1283-1288. With English Translation, 11 pages.

Hanna-Mitchell, A.T. et al. (2014). "Pathophysiology of Idiopathic Overactive Bladder and the Success of Treatment: A Systematic Review From ICI-RS 2013," Neurology and Urodynamics 33:611-617.

Haupt, M. et al. (Sep. 10, 2013, e-pub. Jun. 1, 2013). "Lipid-Based Intravesical Drug Delivery Systems With Controlled Release of Trospium Chloride for the Urinary Bladder," Journal of Controlled Release 170:161-166.

History of Changes for Study: NCT03109379: "Safety and Tolerability of TAR-302-5018 in Subjects With Idiopathic Overactive Bladder," retrieved from URL:https://clinicaltrials.gov/ct2/history/NCT03109379?V_5=View#StudyPageTop, last visited Aug. 25, 2019, 11 pages.

Kauth, T. et al. (Sep. 2011). "Embedding of Trospium Chloride in Expanded Foam Spheres to Achieve a Controlled Release Kinetic," Urologe 50(Suppl. 1):88, 1 page.

Kurosch, M. et al. (Mar. 12, 2015). "Therapy of Overactive Bladder (OAB)," Der Urologe 54(4):567-576. With English Translation, 16 pages.

Lee, Y.-S. et al. (Sep. 2011). "Symptom Change After Discontinuation of Successful Antimuscarinic Treatment in Patients With Overactive Bladder Symptoms: A Randomised, Multicentre Trial," Int. J. Clin. Pract. 65(9):997-1004.

Marcelissen, T. et al. (2018). "Management of Idiopathic Overactive Bladder Syndrome: What is Optimal Strategy After Failure of Conservative Treatment?," European Urology Focus 4:760-767.

Michaeli, W. et al. (2009). "Development of an Active Agent Carrying, Biodegradable Implant for the Intravesical Therapy of the Overactive Bladder Syndrome," Annual Technical Conference—ANTEC, Conference Proceedings. 5:2951-2956.

Onur, R. et al. (2010). "Effects of Combined Use of Trosplum Chloride and Melatonin on In Vitro Contractility of Rat Urinary Bladder," Bladder Physiology 75:873-878.

Tyagi, P. et al. (No Date). "Chapter 10—The Overactive Bladder: Evaluation and Management," Drug Delivery and Intraversical Instillation pp. 115-124.

U.S. Appl. No. 14/224,256, filed Mar. 25, 2014, by Cima et al. (Copy not submitted herewith pursuant to the waiver of 37 C.F.R. § 1.98(a)(2)(iii) issued by the Office on Sep. 21, 2004.).

Von Walter, M. et al. (2009). "Trospium Chloride Released from Intravesically Applied PLGA-Based Carries Decreased Bladder Contractility in an Isolated Whole Pig Bladder Model," Eur. Urol. Suppl. 9(4):176, Abstract 230, 1 page.

Walter, P. et al. (1999). "Bioavailability of Trospium Chloride After Intravesical Instillation in Patients with Neurogenic Lower Urnary Tract Dysfunction: A Pilot Study," Neurourology and Urodynamics 18:447-453.

Wiedemann, A. et al. (2007). "Antimuscarinic Drugs for the Treatment of Overactive Bladder Are They really all the same?—A Comparative Review of Data Pertaining to Pharmacological and Physiological Aspects," 9(Suppl. 1):29-42.

Krivoborodov, G.G. et al. (Aug. 2016). "High Doses of Trospium Chloride in Patients with Idiopathic Overactive Bladder. Data of Large-Scale, Multicenter Observational Program 'Resource'," Urologila 4, 13 pages. Machine Translation.

Krivoborodov, G.G. et al. (Aug. 2016). "Trosplum Chloride in the Treatment of Overactive Bladder in Elderly Patients with Neurological Diseases (Data Multicenter Observational Program "Resource")," Medical Advice 18(7):55-59, 10 pages. Machine Translation.

Kuznetsov, S.A. (2000). "Great Explanatory of the Russian Language," Bogdfanova, I. A. ed., The Russian Academy of Sciences Institute For Linguistic Studies: Saint Petersburg, Russia, 6 pages. English Translation.

Harkevich, D. A. et al. (2005). "Pharmacology with General Formulation: Effect on the Properties of Drugs and the Conditions of their Application," 2nd Edition, Moscow, p. 41, 6 pages. Machine Translation.

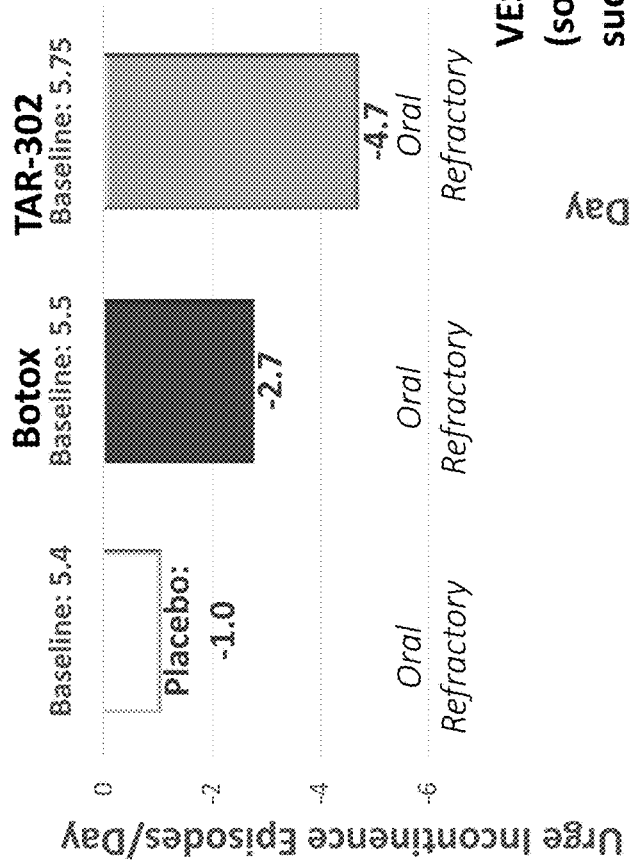
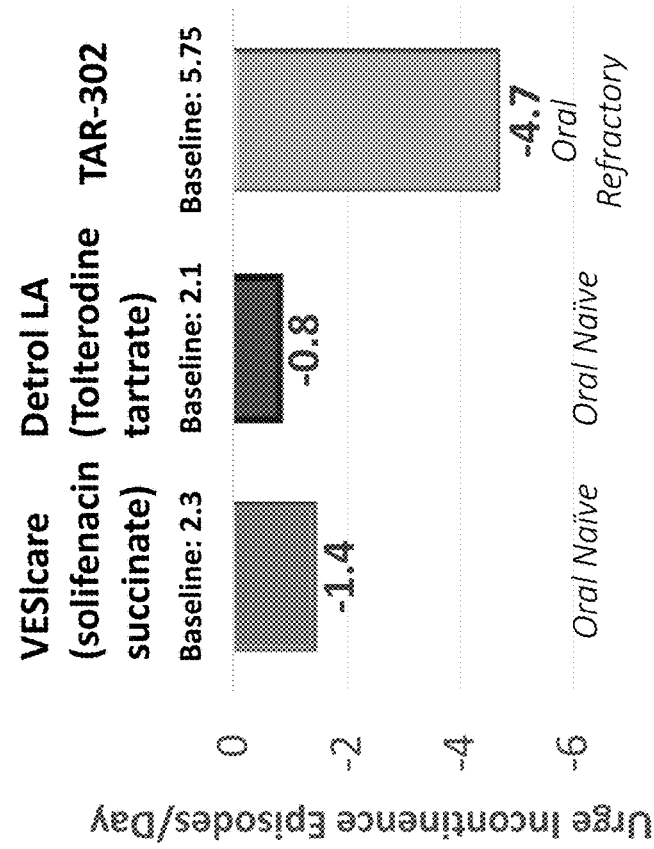
FIG. 10A
FIG. 10B

FIG. 13

OAB-q Short Form

This questionnaire asks about how much you have been bothered by selected bladder symptoms during the past 4 weeks. Please place a ✓ or x in the box that best describes the extent to which you were bothered by each symptom during the past 4 weeks. There are no right or wrong answers. Please be sure to answer every question.

| During the past 4 weeks, how bothered were you by ... | Not at all | A little bit | Some-what | Quite a bit | A great deal | A very great deal |
|---|---|---|---|---|---|---|
| 1. An uncomfortable urge to urinate? | ☐ 1 | ☐ 2 | ☐ 3 | ☐ 4 | ☐ 5 | ☐ 6 |
| 2. A sudden urge to urinate with little or no warning? | ☐ 1 | ☐ 2 | ☐ 3 | ☐ 4 | ☐ 5 | ☐ 6 |
| 3. Accidental loss of small amounts of urine? | ☐ 1 | ☐ 2 | ☐ 3 | ☐ 4 | ☐ 5 | ☐ 6 |
| 4. Nighttime urination? | ☐ 1 | ☐ 2 | ☐ 3 | ☐ 4 | ☐ 5 | ☐ 6 |
| 5. Waking up at night because you had to urinate? | ☐ 1 | ☐ 2 | ☐ 3 | ☐ 4 | ☐ 5 | ☐ 6 |
| 6. Urine loss associated with a strong desire to urinate? | ☐ 1 | ☐ 2 | ☐ 3 | ☐ 4 | ☐ 5 | ☐ 6 |

FIG. 14

For the following questions, please think about your overall bladder symptoms in the past 4 weeks and how these symptoms have affected your life. Please answer each question about how often you have felt this way to the best of your ability. Please place a ✓ or × in the box that best answers each question.

| During the past 4 weeks, how often have your bladder symptoms ... | None of the time | A little of the time | Some of the time | A good deal of the time | Most of the time | All of the time |
|---|---|---|---|---|---|---|
| 1. Caused you to plan "escape routes" to restrooms in public places? | ☐ 1 | ☐ 2 | ☐ 3 | ☐ 4 | ☐ 5 | ☐ 6 |
| 2. Made you feel like there is something wrong with you? | ☐ 1 | ☐ 2 | ☐ 3 | ☐ 4 | ☐ 5 | ☐ 6 |
| 3. Interfered with your ability to get a good night's rest? | ☐ 1 | ☐ 2 | ☐ 3 | ☐ 4 | ☐ 5 | ☐ 6 |
| 4. Made you frustrated or annoyed about the amount of time you spend in the restroom? | ☐ 1 | ☐ 2 | ☐ 3 | ☐ 4 | ☐ 5 | ☐ 6 |
| 5. Made you avoid activities away from restrooms (i.e., walks, running, hiking)? | ☐ 1 | ☐ 2 | ☐ 3 | ☐ 4 | ☐ 5 | ☐ 6 |
| 6. Awakened you during sleep? | ☐ 1 | ☐ 2 | ☐ 3 | ☐ 4 | ☐ 5 | ☐ 6 |
| 7. Caused you to decrease your physical activities (exercising, sports, etc.)? | ☐ 1 | ☐ 2 | ☐ 3 | ☐ 4 | ☐ 5 | ☐ 6 |
| 8. Caused you to have problems with your partner or spouse? | ☐ 1 | ☐ 2 | ☐ 3 | ☐ 4 | ☐ 5 | ☐ 6 |
| 9. Made you uncomfortable while traveling with others because of needing to stop for a restroom? | ☐ 1 | ☐ 2 | ☐ 3 | ☐ 4 | ☐ 5 | ☐ 6 |
| 10. Affected your relationships with family and friends? | ☐ 1 | ☐ 2 | ☐ 3 | ☐ 4 | ☐ 5 | ☐ 6 |
| 11. Interfered with getting the amount of sleep you needed? | ☐ 1 | ☐ 2 | ☐ 3 | ☐ 4 | ☐ 5 | ☐ 6 |
| 12. Caused you embarrassment? | ☐ 1 | ☐ 2 | ☐ 3 | ☐ 4 | ☐ 5 | ☐ 6 |
| 13. Caused you to locate the closet restroom as soon as you arrive at a place you have never been? | ☐ 1 | ☐ 2 | ☐ 3 | ☐ 4 | ☐ 5 | ☐ 6 |

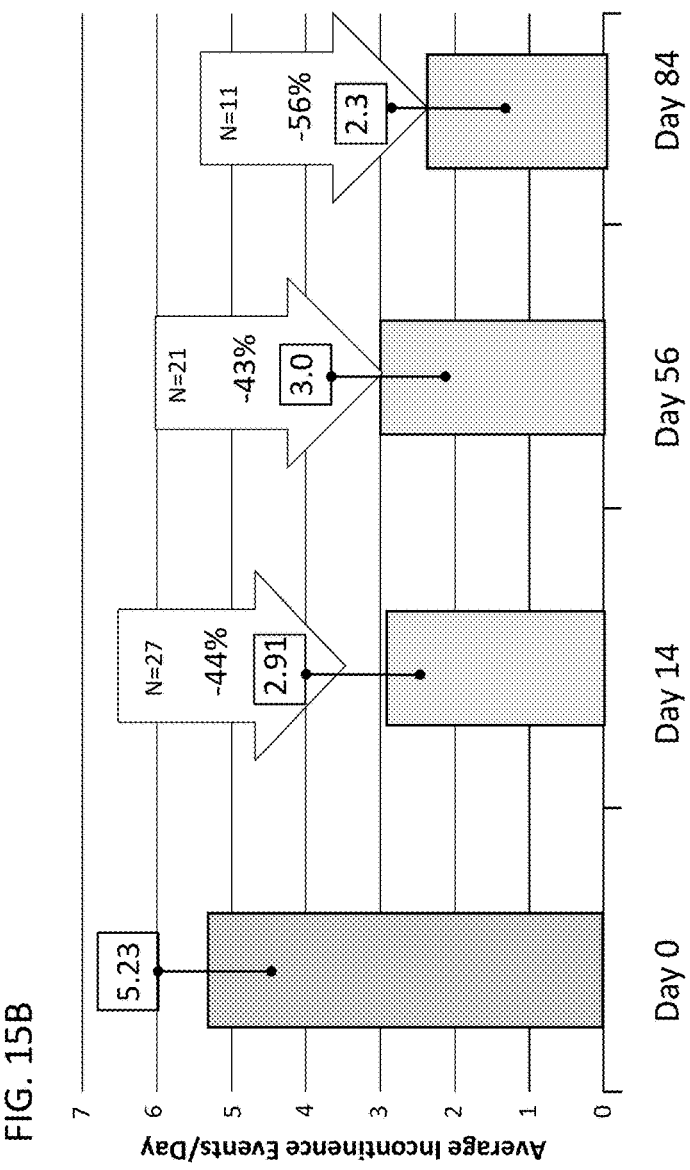
FIG. 15A
FIG. 15B

METHODS OF TREATING OVERACTIVE BLADDER USING TROSPIUM

CROSS REFERENCE TO RELATED APPLICATIONS

This application is a continuation of U.S. patent application Ser. No. 16/528,032, filed Jul. 31, 2019, which claims the benefit of, and priority to U.S. provisional application 62/713,414, filed Aug. 1, 2018 and U.S. provisional application 62/850,481 filed May 20, 2019, entitled "METHODS OF TREATING OVERACTIVE BLADDER USING TROSPIUM," the contents of each of which is incorporated herein by reference in its entirety.

TECHNICAL FIELD

The present application relates to methods of treating overactive bladder, training or retraining bladder, prolonging symptom relief, improving the quality of life and/or neuronal remodeling in an individual having overactive bladder, by locally delivering trospium to the bladder.

BACKGROUND

Lower urinary tract disorders, including overactive bladder, detrusor instability, and urinary incontinence can arise from numerous pathologies. These pathologies are commonly classified as neuropathic, myogenic, or idiopathic. The majority of patients usually are characterized as idiopathic due to the lack of observable disease etiology.

Recent studies have suggested the sensory system of the urothelium may play an important role in afferent signaling and detrusor activity. See de Groat and Yoshimura, Handb Exp Pharmacol. 2009; (194): 91-138; Daly et al. Current Opinion in Urology 2011, 21:268-274; Birder and Andersson Physiol Rev 93: 653-680, 2013. Pathologies of this system have been suggested to play a significant role in many patients with lower urinary tract idiopathic disease.

Standard drug therapies for patients with idiopathic lower urinary tract disorders are systemic treatments typically administered orally or trans-dermally. These therapies often lack adequate efficacy due to either dose limiting side effects, low potency, or both.

Currently patients failing systemic drug therapy have only two alternatives. The first alternative is Botox injections directly into the bladder wall, which may provide symptom relief, but which also undesirably can produce prolonged urinary retention requiring self-catheterization. The second alternative is neurosacral stimulation as produced by the InterStim® device which is surgically implanted and shown to provide symptomatic relief. However, the equipment and surgical procedure is expensive, highly invasive, and carries a 30% adverse event rate requiring corrective surgeries or removals.

Overactive bladder is a chronic condition characterized by the lower urinary tract symptoms of urinary urgency, with or without urge incontinence, usually with urinary frequency and nocturia. Overactive bladder is the most common cause of urinary incontinence or loss of bladder control in adults and affects approximately 33 million, or about 17%, of adults in the U.S.A. Although the prevalence among men and women in the U.S.A. is similar (16.0% vs. 16.9%, respectively), the severity and nature of symptom expression does differ, with women demonstrating a higher incidence of urge incontinence. There is also a marked increase in prevalence with increasing age. Overactive bladder has a significant impact on the health-related quality of life, mental health, and quality of sleep of affected individuals; whether or not they display the symptom of urge incontinence. The economic burden of overactive bladder is also significant, estimated at approximately $12 billion per annum in the U.S.A. alone. Overactive bladder is distinct from stress urinary incontinence, but when they occur together is usually known as mixed incontinence.

The urothelial sensory system is comprised of numerous receptors and signaling pathways, many of which exhibit significant "cross talk." Due to the complexity of the urothelial sensory system, selective agents, such as darifenasin, may not adequately modulate urothelial sensory activation following nonspecific noxious stimuli. Similarly, non-specific agents, such as oxybutynin which exhibits antimuscarinic and calcium channel activity, do not inhibit urothelial response as measured by intercontraction intervals but can lead to urinary retention.

Accordingly, there remains a need for more and better treatment options for lower urinary tract disorders, including overactive bladder. Desirably, such treatments would address one or more of the problems associated with systemic administration of drugs and with highly invasive and expensive surgical procedures. Desirably, the treatment would also avoid or lessen the need for painful injections and repeated self-catheterization. Desirably, the treatment would generate a sustainable response.

The disclosures of all publications, patents, patent applications and published patent applications referred to herein are hereby incorporated herein by reference in their entirety.

SUMMARY

In some embodiments, provided herein is a method of training the bladder of an individual having overactive bladder comprising administering an effective amount of trospium locally to the bladder of the individual for at least about 24 hours.

In some embodiments, provided herein is a method of prolonging symptom relief for an individual having overactive bladder comprising administering an effective amount of trospium locally to the bladder for at least about 24 hours, wherein the individual experiences relief of a symptom for at least about 24 hours after trospium administration is completed.

In some embodiments, provided herein is a method of improving the quality of life of an individual having overactive bladder comprising administering an effective amount of trospium locally to the bladder for at least about 24 hours, wherein the quality of life of the individual is improved upon treatment with trospium.

In some embodiments according to any of the methods described above, the individual having overactive bladder experiences at least about 50% of baseline symptom relief for at least about 7 days after trospium administration is completed.

In some embodiments according to any of the methods described above, trospium is continuously administered locally to the bladder for at least about 42 days.

In some embodiments according to any of the methods described above, the method further comprises administering an effective amount of trospium locally to the bladder about every 3 months or on an as needed (prn) basis.

In some embodiments, provided herein is method of treating overactive bladder comprising continuously administering an effective amount of trospium locally to the bladder of the individual for at least about 42 days.

In some embodiments according to any of the methods described above, trospium is continuously administered for about 56 days, or about 12 weeks. In some embodiments, trospium is continuously administered for at least about 12 weeks.

In some embodiments also provided herein is a method of maintenance therapy for overactive bladder in an individual comprising administering trospium continuously and locally to the bladder for at least about 24 hours, wherein the individual has received a previous therapy for overactive bladder. In some embodiments, the maintenance therapy comprises administering an effective amount of trospium locally to the bladder for at least about 24 hours every 3 months. In some embodiments, the maintenance therapy comprises administering an effective amount of trospium locally to the bladder for at least about 24 hours on an as needed (prn) basis. In some embodiments, the maintenance therapy comprises administering an effective amount of trospium locally to the bladder for at least about 24 hours upon symptom recurrence. In some embodiments, the maintenance therapy comprises administering an effective amount of trospium locally to the bladder for at least about 24 hours when the individual experiences at least a 50% recurrence in baseline symptoms. In some embodiments, the previous therapy comprises administering an effective amount of trospium locally to the bladder for at least about 24 hours, at least about 42 days, at least about 56 days, or at least about 12 weeks.

In some embodiments according to any of the methods described above, the concentration of trospium in the bladder is between about 0.1 to 100 g/ml during administration of trospium. In some embodiments, the concentration of trospium in the plasma of the individual is less than about 2 ng/ml during administration of trospium.

In some embodiments according to any of the methods described above, the individual has idiopathic overactive bladder.

In some embodiments according to any of the methods described above, the individual has multiple sclerosis, Alzheimer's disease, Parkinson's disease, or has previously had a stroke.

In some embodiments according to any of the methods described above, the individual has failed a previous treatment for overactive bladder.

In some embodiments according to any of the methods described above, the individual has not received a previous treatment for overactive bladder.

In some embodiments according to any of the methods described above, the individual has failed or is not eligible for oral therapy.

In some embodiments according to any of the methods described above, the individual has urinary incontinence or urge incontinence.

In some embodiments according to any of the methods described above, the method results in neuronal remodeling or remodeling of a neural network. In some embodiments, symptomatic relief of urgency, frequency, or incontinence is achieved. In some embodiments, the quality of life score of the individual is improved. In some embodiments, the urinary bother score of the individual is reduced. In some embodiments, the method reduces an aberrant urge to urinate.

In some embodiments according to any of the methods described above, trospium is administered to the bladder by using an intravesical device.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIG. 12A is a plan view. FIG. 12B is a cross-sectional view taken along line 3-3 in FIG. 12A. FIG. 12C is a view of one end portion of the device disposed within the working channel of a deployment instrument, which is shown in partial cross-section.

FIG. 10A and FIG. 10B show the efficacy of overactive bladder treatments. FIG. 10A shows the change in daily urge incontinence episodes in oral-refractory overactive bladder patients at the end of dosing after treatment of TAR-302 or Botox®. FIG. 10B shows the reduction in daily urge incontinence episodes in oral naïve overactive bladder patients after treatment of VESIcare® (solifenacin succinate) or Detrol® LA (tolterodine tartrate) as compared to the reduction in daily urge incontinence episodes in oral-refractory patients after treatment of TAR-302.

FIG. 13 shows exemplary questionnaire for evaluating bother score.

FIG. 14 shows exemplary questionnaire for evaluating quality of life score.

FIGS. 15A and 15B show the scheme of the study (FIG. 15A) and average daily incontinence episodes assessed at Day 0 (baseline), Day 14, Day 56 and Day 84 after the insertion of TAR-302 (FIG. 15B).

DETAILED DESCRIPTION

Figure 1A:
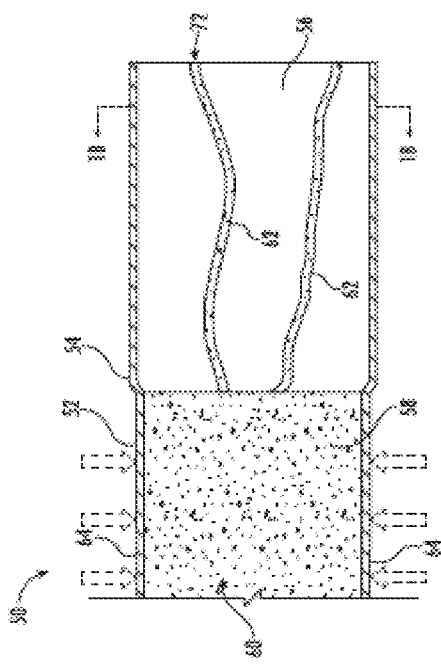
FIG. 1A is a cross-sectional side view of one embodiment of an elastic portion of a device containing a restraining end plug.
Figure 1B:
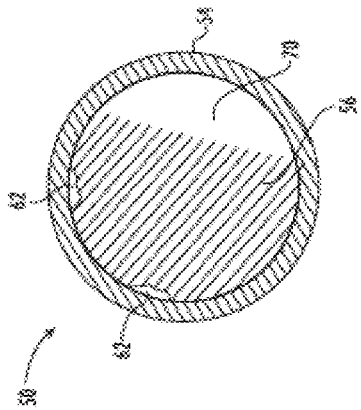
FIG. 1B is a cross-sectional end view of the embodiment of FIG. 1A.
Figure 1C:
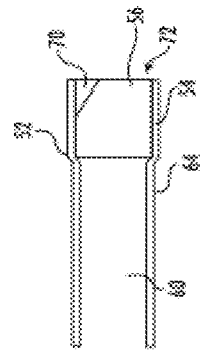
FIG. 1C is a cross-sectional side view of the device of FIG. 1A when the reservoir is not under an osmotic pressure.
Figure 1D:
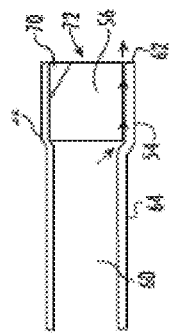
FIG. 1D is a cross-sectional side view of the device of FIG. 1A when the reservoir is under an osmotic pressure.

The present application is at least partly based upon Applicant's striking finding that administering an effective amount of trospium locally (e.g., intravesically) into the bladder of an individual having overactive bladder can result in prolonged symptom relief (e.g., reduced urinary incontinence). In a phase I clinical trial TAR-302, a passive, nonresorbable trospium-releasing intravesical system whose primary mode of action is the controlled release of trospium into the bladder over a period of about 42 days, was shown not only to reduce incontinence episodes during the 42 days during which trospium was administered to the bladder but also surprisingly and significantly reduced incontinence episodes in the six weeks after trospium administration was terminated. The present methods has substantial benefits over previous methods of bladder treatment including oral therapy with trospium, such as reduced side effects along with a higher concentration of trospium locally in the bladder. Thus in some aspects, the present invention is especially suitable for individuals who have idiopathic overactive bladder, have failed oral therapy, and/or have severe recalcitrant disease. In some aspects, the present application provides methods of training or retraining the bladder of an individual having overactive bladder. In some aspects, the present application provides methods of prolonging symptom relief for an individual having overactive bladder. In some aspects, the present application provides methods of neuronal remodeling in an individual having overactive bladder. In some aspects, the present application provides methods of improving the quality of life in an individual having overactive bladder.

Definitions

As used herein, the singular forms "a," "an," and "the" include plural referents unless the context clearly dictates otherwise. For example, "a" or "an" means "at least one" or "one or more."

The term "individual" as used herein refers to a mammal, including humans. An individual includes, but is not limited to, human, bovine, horse, feline, canine, rodent, or primate. In some embodiments, the individual is human.

The term "effective amount" used herein refers to an amount of a compound or composition sufficient to treat a specified disorder, condition or disease such as to ameliorate, palliate, lessen, and/or delay one or more of its symptoms.

Reference to "about" a value or parameter herein includes (and describes) embodiments that are directed to that value or parameter per se. For example, "about 7 days" includes 7 days.

The term "about X-Y" used herein has the same meaning as "about X to about Y." Similarly, "about X to Y" used herein has the same meaning as "about X to about Y."

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the recurrence of the disease, delaying or slowing the progression of the disease, ameliorating the disease state, decreasing the dose of one or more other medications required to treat the disease, delaying the progression of the disease, and/or increasing or improving the quality of life. The methods of the invention contemplate any one or more of these aspects of treatment.

Methods

The present application in one aspect provides a method of training (or retraining) the bladder of an individual having overactive bladder comprising administering an effective amount of trospium locally to the bladder of the individual for at least about 24 hours. In some embodiments, trospium is administered for at least about 3, 5, or 7 days. In some embodiments, trospium is administered for at least about 2, 3, 4, 5, 6, 7, 8, 9, 10, 11, 12, 13, 14, 15, or 16 weeks. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL during trospium administration. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application also provides a method of training (or retraining) the bladder of an individual having overactive bladder comprising administering an effective amount of trospium locally to the bladder of the individual for at least about 42 days (e.g., about 42, 56, 70, or 84 days). In some embodiments, trospium is administered for at least about 56 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application also provides a method of training (or retraining) the bladder of an individual having overactive bladder comprising administering an effective amount of trospium locally to the bladder of the individual for at least about 42 days (e.g., about 42, 56, 70, or 84 days), wherein the individual has had a prior therapy, and wherein the individual is refractory to the prior therapy. In some embodiments, trospium is administered for at least about 56 days. In some embodiments, trospium is administered for at least about 84 days. In some embodiments, trospium is administered for at least about 100 days. In some embodiments, the prior therapy is an oral therapy. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of prolonging symptom relief for an individual having overactive bladder comprising administering an effective amount of trospium locally to the bladder for at least about 24 hours, wherein the individual experiences relief of a symptom for at least about 24 hours after trospium administration is completed. In some embodiments, a prolonged symptom relief of urgency, frequency, urinary incontinence and/or urge incontinence is achieved. In some embodiments, the individual experiences relief of a symptom for at least about 1, 2, 3, 4, 5, or 6 weeks after trospium administration is completed. In some embodiments, trospium is administered for at least about 3, 5, or 7 days. In some embodiments, trospium is administered for at least about 2, 3, 4, 5, 6, 7, 8, 9, 10, 11, 12, 13, 14, 15, or 16 weeks. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application also provides a method of prolonging symptom relief for an individual having overactive bladder comprising administering an effective amount of trospium locally to the bladder for at least about 42 days (e.g., about 42, 56, 70, or 84 days), wherein the individual experiences relief of a symptom for at least about 24 hours after trospium administration is completed. In some embodiments, a prolonged symptom relief of urgency, frequency, urinary incontinence and/or urge incontinence is achieved. In some embodiments, the individual experiences relief of a symptom for at least about 1, 2, 3, 4, 5, or 6 weeks after trospium administration is completed. In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application also provides a method of prolonging symptom relief for an individual having overactive bladder comprising administering an effective amount of trospium locally to the bladder for at least about 42 days (e.g., about 42, 56, 70, or 84 days), wherein the individual experiences relief of a symptom for at least about 24 hours after trospium administration is completed (such as at least about 2, 5, 7, 10, 15, 20, 25, 30, 35, 40 days after the completion of trospium administration), wherein the individual has a prior therapy, and wherein the individual is refractory to the prior therapy. In some embodiments, a prolonged symptom relief of urgency, frequency, urinary incontinence and/or urge incontinence is achieved. In some embodiments, the individual experiences relief of a symptom for at least about 1, 2, 3, 4, 5, or 6 weeks after trospium administration is completed. In some embodiments, trospium is administered for at least about 56 days. In some embodiments, trospium is administered for at least about 84 days. In some embodiments, trospium is administered for at least about 100 days. In some embodiments, the prior therapy is an oral therapy. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of neuronal remodeling in an individual having overactive bladder comprising administering an effective amount of trospium locally to the bladder for at least about 24 hours, wherein the neuronal remodeling persists for at least about 24 hours after trospium administration is completed (such as at least about 2, 5, 7, 10, 15, 20, 25, 30, 35, 40 days after the completion of trospium administration). In some embodiments, trospium is administered for at least about 3, 5, or 7 days. In some embodiments, trospium is administered for at least about 2, 3, 4, 5, 6, 7, 8, 9, 10, 11, 12, 13, 14, 15, or 16 weeks. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of neuronal remodeling in an individual having overactive bladder comprising administering an effective amount of trospium locally to the bladder for at least about 42 days (e.g., about 42, 56, 70, or 84 days), wherein the neuronal remodeling persists for at least about 24 hours after trospium administration is completed (such as at least about 2, 5, 7, 10, 15, 20, 25, 30, 35, 40 days after the completion of trospium administration). In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of neuronal remodeling in an individual having overactive bladder comprising administering an effective amount of trospium locally to the bladder for at least about 42 days (e.g., about 42, 56, 70, or 84 days), wherein the neuronal remodeling persists for at least about 24 hours after trospium administration is completed (such as at least about 2, 5, 7, 10, 15, 20, 25, 30, 35, 40 days after the completion of trospium administration), wherein the individual has a prior therapy, and wherein the individual is refractory to the prior therapy. In some embodiments, trospium is administered for at least about 56 days. In some embodiment, trospium is administered for at least about 56 days. In some embodiments, trospium is administered for at least about 100 days. In some embodiments, the prior therapy is an oral therapy. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of improving the quality of life in an individual having overactive bladder comprising administering an effective amount of trospium locally to the bladder for at least about 24 hours, wherein the quality of life of the individual is improved at least about 24 hours after trospium administration is completed. In some embodiments, the individual has an improved quality of life score. In some embodiments, the individual has a reduced urinary bother score. In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke. In some embodiments, the individual has had an intravesicular device.

The present application in another aspect provides a method of improving the quality of life in an individual having overactive bladder comprising administering an effective amount of trospium locally to the bladder for at least about 42 days (e.g., about 42, 56, 70, or 84 days), wherein the quality of life is improved for at least about 24 hours after trospium administration is completed (such as at least about 2, 5, 7, 10, 15, 20, 25, 30, 35, 40 days after the completion of trospium administration). In some embodiments, the individual has an improved quality of life score. In some embodiments, the individual has a reduced urinary bother score. In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke. In some embodiments, the individual has had an intravesicular device.

The present application in another aspect provides a method of improving the quality of life in an individual having overactive bladder comprising administering an effective amount of trospium locally to the bladder for at least about 42 days (e.g., about 42, 56, 70, or 84 days), wherein the quality of life is improved at least about 24 hours after trospium administration is completed, wherein the individual has a prior therapy, and wherein the individual is refractory to the prior therapy. In some embodiments, the individual has an improved quality of life score. In some embodiments, the individual has a reduced urinary bother score. In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke. In some embodiments, the individual has had an intravesicular device.

Also provided herein is a method of increasing the quality of life score in an individual comprising administering an effective amount of trospium locally to the bladder for at least about 42 days (e.g., about 42, 56, 70, or 84 days), wherein the quality of life is improved at least about 24 hours after trospium administration is completed. In some embodiments, improvement of quality of life is measured as an improved quality of life score. In some embodiments, improvement of quality of life is measured as a reduced urinary bother score. In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke. In some embodiments, the individual has had an intravesicular device.

Provided herein is a method of reducing the urinary bother score in an individual, comprising administering an effective amount of trospium locally to the bladder for at least about 42 days (e.g., about 42, 56, 70, or 84 days), wherein the quality of life is improved at least about 24 hours after trospium administration is completed. In some embodiments, improvement of quality of life is measured as an improved quality of life score. In some embodiments, improvement of quality of life is measured as a reduced urinary bother score. In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered for at least about 84 days. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke. In some embodiments, the individual has had an intravesicular device.

The present application in another aspect provides a method of treating overactive bladder comprising continuously administering an effective amount of trospium locally to the bladder of the individual for at least about 42 days (e.g., about 42, 56, 70, or 84 days). In some embodiments, trospium is administered for at least about 56 days. In some embodiments, trospium is administered for at least about 84 days. In some embodiments, trospium is administered for at least about 100 days. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual has a prior therapy for overactive bladder. In some embodiments, the prior therapy is an oral therapy. In some embodiments, the individual does not respond or is refractory to the prior therapy. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of treating overactive bladder comprising continuously administering an effective amount of trospium locally to the bladder of the individual for at least about 42 days (e.g., about 42, 56, 70, or 84 days), wherein the individual has a prior therapy, and wherein the individual is refractory to the prior therapy. In some embodiments, trospium is administered for at least about 56 days. In some embodiments, trospium is administered for at least about 84 days. In some embodiments, trospium is administered for at least about 100 days. In some embodiments, the prior therapy is an oral therapy. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

The present application in another aspect provides a method of maintenance therapy for overactive bladder in an individual comprising administering trospium continuously and locally to the bladder for at least about 24 hours, wherein the individual has received a previous therapy for overactive bladder. In some embodiments, the maintenance therapy comprises administering an effective amount of trospium locally to the bladder for at least about 24 hours every 3 months. In some embodiments, the maintenance period comprises administering an effective amount of trospium locally to the bladder for at least about 24 hours on an as needed (prn) basis. In some embodiments, the maintenance therapy comprises administering an effective amount of trospium locally to the bladder for at least about 24 hours upon symptom reoccurrence. In some embodiments, the maintenance therapy comprises administering an effective amount of trospium locally to the bladder for at least about 24 hours when the individual experiences at least a 50% recurrence in baseline symptoms. In some embodiments, the previous therapy comprises administering an effective amount of trospium locally to the bladder for at least about 24 hours, at least about 42 days, at least about 56 days, or at least about 84 days. In some embodiments, the prior therapy is an oral therapy. In some embodiments, the individual is refractory to the prior therapy. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

Provided herein is a method maintenance therapy for overactive bladder in an individual comprising administering trospium continuously and locally to the bladder for at least about 24 hours on a prn (as needed) basis, wherein the individual has received a previous therapy for overactive bladder. In some embodiments the maintenance therapy comprises administering tropism locally to the bladder for at least about 42 days, at least about 56 days, or at least about 84 days. In some embodiments the prior therapy is an oral therapy. In some embodiments, the prior therapy comprises local administration of trospium to the bladder. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

Also provided herein is a method maintenance therapy for overactive bladder in an individual comprising administering trospium continuously and locally to the bladder for at least about 24 hours on a quarterly basis, wherein the individual has received a previous therapy for overactive bladder. In some embodiments the maintenance therapy comprises administering tropism locally to the bladder for at least about 42 days, at least about 56 days, or at least about 84 days. In some embodiments the prior therapy is an oral therapy. In some embodiments, the prior therapy comprises local administration of trospium to the bladder. In some embodiments, trospium is administered by using an intravesical delivery device. In some embodiments, trospium is administered at a dose of about from 1 mg/day to 100 mg/day, from about 1 mg/day to 20 mg/day, from about 2 mg/day to 10 mg/day, from about 4 mg/day to about 8 mg/day. In some embodiments, the concentration of trospium in the urine is about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, trospium is administered continuously or intermittently. In some embodiments, the individual having overactive bladder experiences at least about 50% of baseline symptom relief for at least about 7 days, 2 weeks, 3 weeks, 4 weeks, 5 weeks, or 6 weeks after trospium administration is completed. In some embodiments, the individual is human. In some embodiments, the individual has idiopathic overactive bladder. In some embodiments, the individual has multiple sclerosis, Alzheimer's disease, Parkinson's disease, or has previously had a stroke.

Trospium

Trospium is a muscarinic receptor antagonist. It is known for use in the treatment of overactive bladder, where it is formulated for oral administration, e.g., Sanctura™ (Allergan). As with other oral muscarinic receptor antagonists, patients often experience dose limiting side effects or inadequate efficacy. In the present application, trospium is formulated for local delivery. It may be provided in solid or semi-solid form or in a liquid form, depending on the delivery mechanism employed, as described herein. In some embodiments, devices, and systems described herein, trospium is provided in the form of a pharmaceutically acceptable salt of trospium. In some embodiments, the pharmaceutically acceptable salt of trospium is trospium chloride. In some embodiments, other suitable form of trospium is used, including but not limited to a polymorph, a hydrate, etc.

In some embodiments, trospium is the compound 3-(2-hydroxy-2,2-diphenylacetoxy)spiro[bicyclo[3.2.1]octane-8,1'-pyrrolidin]-1'-ium chloride and any pharmaceutically-acceptable salt thereof. The chemical formula is given in formula I.

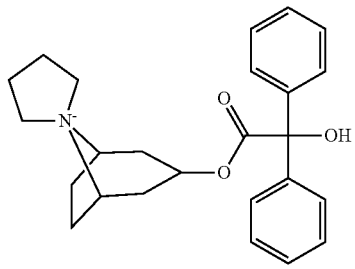

Dosage Regimens

The following section describes various aspects (embodiments) of dosing and treatment regimens, any and all of which apply to the methods described herein.

In various embodiments, trospium is administered locally to the bladder (e.g., intravesically) in a dosage amount from about 0.075 mg/day to about 150 mg/day, such as from about 0.15 mg/day to 150 mg/day, from about 1 mg/day to 100 mg/day, from about 1 mg/day to 20 mg/day, from about 2 mg/day to 10 mg/day, from about 4 mg/day to about 8 mg/day over the treatment period. In some embodiments, trospium is administered locally to the bladder (e.g., intravesically) in a dosage amount no more than about 60 mg/day, 40 mg/day, 20 mg/day, 15 mg/day, 10 mg/day or 8 mg/day over the treatment period. In some embodiments, trospium is administered locally to the bladder (e.g., intravesically) in a dosage amount no less than about 0.1 mg/day, 0.5 mg/day, 1 mg/day, 2 mg/day, 3 mg/day, 4 mg/day.

In some embodiments, trospium is administered locally to the bladder (e.g., intravesically) of an individual for at least about 24 hours, 2 days, 3 days, 4 days, 5 days, 6 days, or 7 days. In some embodiments, trospium is administered locally to the bladder (e.g., intravesically) of an individual for at least about 1, 2, 3, 4, 5, 6, 7, 8, 9, 10, 11, 12, 13, 14, 15, or 16 weeks. In some embodiments, trospium is administered locally to the bladder (e.g., intravesically) of an individual for at least about 6 weeks, or 42 days. In some embodiments, trospium is administered locally to the bladder (e.g., intravesically) of an individual for at least about 8 weeks, or 56 days. In some embodiments, trospium is administered locally to the bladder for at least about 12 weeks, or 84 days. In some embodiments, trospium is administered locally to the bladder (e.g., intravesically) of an individual for at least 16 weeks, or 112 days. In some embodiments, trospium is administered locally to the bladder (e.g., intravesically) of an individual for at least about 1, 2, 3, 4, 5, 6, 7, 8, 9, 10, 11, or 12 months. In some embodiments, trospium is administered locally to the bladder (e.g., intravesically) of an individual for at least about 10, 20, 30, 40, 50, 60, 70, 80, 90, or 100 days. In some embodiments, trospium is administered locally to the bladder (e.g., intravesically) of an individual for about 7 days, 14 days, 21 days, 28 days, 35 days, 42 days, 49 days, 56 days, 63 days, 70 days, 77 days, 84 days, 91 days, 98 days, 105 days, or 112 days.

In some embodiments, trospium is administered locally to the bladder (e.g., intravesically) of an individual for at least about 24 hours, 2 days, 3 days, 4 days, 5 days, 6 days, or 7 days every one, two, three, four five or six weeks. In some embodiments, trospium is administered locally to the bladder (e.g., intravesically) of an individual for at least about 24 hours, 2 days, 3 days, 4 days, 5 days, 6 days, or 7 days every one, two, three, four, five or six months. In some embodiments, trospium is administered locally to the bladder (e.g., intravesically) of an individual for at least about one week, two weeks, three weeks or four weeks every one, two, three, four, five or six months. In some embodiments, trospium is administered locally to the bladder (e.g., intravesically) of an individual for at least about five weeks or six weeks every two, three, four, five or six months.

In some embodiments, trospium is administered locally (e.g., intravesically) into the individual's bladder at a mean average amount of from 1 mg/day to 100 mg/day, for example, from 1 mg/day to 20 mg/day, from 2 mg/day to 10 mg/day, from 4 mg/day to about 8 mg/day for up to about 7, 14, 21, 28, 35, 42 days, 49 days, 56 days, 63 days, 70 days, 77 days, 84 days, 91 days, 98 days, 105 days, or 112 days. In some embodiments, trospium is administered locally (e.g., intravesically) into the individual's bladder at a mean average amount of from 1 mg/day to 100 mg/day, for example, from 1 mg/day to 20 mg/day, from 2 mg/day to 10 mg/day, from 4 mg/day to about 8 mg/day for up to about 6, 7, 8, 9, 10, 11, or 12 months.

In some embodiments, trospium is administered locally (e.g., intravesically) into the individual's bladder at a mean average amount of about 10 mg/day for about 40-45 days (such as about 42 days). In some embodiments, trospium is administered locally (e.g., intravesically) into the individual's bladder at a mean average amount of about 10 mg/day for about 80-87 days (such as about 84 days). In some embodiments, trospium is only administered once.

In some embodiments, the concentration of trospium in the urine is about or at least about 0.01, 0.05, 0.1, 0.5, 1, 2, 3, 4, 5, 6, 7, or 8 µg/mL while trospium is administered. In some embodiments, the concentration of trospium in the urine is about 2-3 µg/mL, about 3-4 µg/mL, about 4-5 µg/mL, about 5-6 µg/mL, or about 6-7 µg/mL while trospium is administered. In some embodiments, the concentration of trospium in the urine is about 0.01 to about 100 µg/mL, for example, about 0.1 µg/mL to about 20 µg/mL, about 1 µg/mL to about 10 µg/mL, about 2 µg/mL to about 8 µg/mL, about 3 µg/mL to about 7 µg/mL, or about 3 µg/mL to about 5 µg/mL while trospium is administered. In some embodiments, the average concentration of trospium in the urine is at least about 0.01, 0.1, 1, 2, 3, 4, 5, 6, 7, 8, 9, or 10 µg/mL while trospium is administered. In some embodiments, the average concentration of trospium in the urine is about 0.01 to about 100 µg/mL, about 0.1 µg/mL to about 20 µg/mL, about 1 µg/mL to about 10 µg/mL, or about 2 µg/mL to about 8 µg/mL, about 3 µg/mL to about 7 µg/mL, or about 3 µg/mL to about 5 µg/mL while trospium is administered. In some embodiments, the plasma concentration of trospium is less than about 2, 1, 0.9, 0.8, 0.7, 0.6, 0.5, 0.4, 0.3, 0.2, or 0.1 ng/ml. In some embodiments, the plasma concentration of trospium is less than about 0.7 ng/ml. In some embodiments, the plasma concentration of trospium not detectable.

In some embodiments, trospium is administered to the bladder via an intravesical delivery device. In some embodiments, the device contains an amount of about 100 mg to 2000 mg trospium (such as about 200 mg to about 1600 mg, about 400 mg to about 1200 mg, about 600 mg to about 1000 mg, about 700 mg to about 900 mg, or about 850 mg trospium). In some embodiments, the device is kept in the individual for at least about one, two, three, four, five or six weeks. In some embodiments, the device is kept in the individual for at least about 8, 10, or 12 weeks. In some embodiments, the device contains an amount of about 850 mg trospium and is kept in the individual for about 42 days.

In some embodiments, the device contains an amount of about 850 mg trospium and is kept in the individual for about 84 days.

In some embodiments, the method comprises a maintenance therapy comprising administering an effective amount of trospium locally (e.g., intravesically) into the individual's bladder periodically following a prior therapy. In some embodiments, the maintenance therapy comprises administering trospium as needed. In some embodiments, the maintenance therapy comprises administering trospium monthly, bi-monthly or quarterly. In some embodiments, the maintenance therapy comprises administering trospium no more than 1, 2, 3, 4, 5, 6, 7, 8, 9, 10, 11, or 12 times per year. In some embodiments, the maintenance therapy comprises administering trospium on a schedule agreed by the individual and a doctor. In some embodiments, the maintenance therapy comprises administering trospium when a symptom of overactive bladder is anticipated to return. In some embodiments, the maintenance therapy comprises administering trospium upon symptom recurrence, for example, when at least an about 10%, 20%, 30%, 40%, 50%, 60%, 70%, 80% or 90% recurrence in baseline symptom occurs. In some embodiments, the maintenance period comprises administering trospium for at least about 24 hours, 2 days, 3 days, 4 days, 5 days, 6 days, or 7 days. In some embodiments, the maintenance period comprises administering trospium for at least about 1, 2, 3, 4, 5, 6, 7, 8, 9, 10, 11, 12, 13, 14, 15, or 16 weeks. In some embodiments, the maintenance therapy comprises administering trospium for at least about 1, 2, 3, 4, 5, 6, 7, 8, 9, 10, 11, or 12 months. In some embodiments, the maintenance therapy comprises administering trospium for at least about 10, 20, 30, 40, 50, 60, 70, 80, 90, or 100 days. In some embodiments, the maintenance therapy comprises administering trospium for about 7 days, 14 days, 21 days, 28 days, 35 days, 42 days, 49 days, 56 days, 63 days, 70 days, 77 days, 84 days, 91 days, 98 days, 105 days, or 112 days.

In some embodiments, the prior therapy comprises administering an antimuscarinic agent. In some embodiments, the antimuscarinic agent is locally administered into the bladder (e.g. intravesically) of the individual. In some embodiments, the antimuscarinic agent is orally administered a local treatment into the individual. In some embodiments, the antimuscarinic agent is trospium. In some embodiments, the prior therapy comprises administering an anticholinergic agent. In some embodiments, the prior therapy comprises administering tropsium locally to the bladder for about 42 or about 56 days.

In some embodiments, the maintenance therapy is initiated immediately after or within 24 hours of the completion of the prior therapy. In some embodiments, the maintenance therapy is initiated at least about 1, 2, 3, 4, 5, 6, or 7 days after the completion of the prior therapy. In some embodiments, the maintenance therapy is initiated at least about 1, 2, 3, 4, 5, 6, 7, 8, 9, 10, 11, or 12 weeks after the completion of the prior therapy. In some embodiments, the maintenance therapy is initiated at least about 3, 4, 5, 6, 7, 8, 9, 10, 11, or 12 months after the completion of the prior therapy.

In some embodiments, the concentration of trospium in the urine is at least about 0.01, 0.05, 0.1, 0.5, 1, 2, 3, 4, 5, 6, 7, or 8 µg/mL during the prior therapy and/or the maintenance therapy period. In some embodiments, the concentration of trospium in the urine is about 0.01 µg/mL to about 100 µg/mL, for example, about 0.1 µg/mL to about 20 µg/mL, about 1 µg/mL to about 10 µg/mL, about 2 µg/mL to about 8 µg/mL, about 3 µg/mL to about 7 µg/mL during the prior therapy and/or the maintenance period. In some embodiments, the average concentration of trospium in the urine is at least about 0.01, 0.1, 1, 2, 3, 4, 5, 6, 7, 8, 9, or 10 µg/mL during the prior therapy and/or the maintenance therapy period. In some embodiments, the average concentration of trospium in the urine is about 0.01 µg/mL to about 100 µg/mL, about 0.1 µg/mL to about 20 µg/mL, about 1 µg/mL to about 10 µg/mL, or about 3 µg/mL to about 8 µg/mL during the prior therapy and/or the maintenance therapy period.

In some embodiments, trospium is administered continuously. In some embodiments, trospium is administered intermittingly.

In some embodiments, trospium is administered via an intravesical device, wherein the intravesical device dwells in the bladder for a period of time, such as at least about 24 hours, for example, for at least about 1, 2, 3, 4, 5, 6, 7, 8, 9, 10, 11, or 12 weeks. In some embodiments, the intravesical device dwells in the bladder for at least about 1, 2, 3, 4, 5, or 6 months. In various embodiments, the intravesical device may release trospium continuously or intermittently to achieve a concentration of trospium in the bladder that produces a sustained, therapeutically effective concentration of trospium over a period from about 24 hours to about 6 months, for example from about 24 hours to 7 days, from about 24 hours to two weeks, from about 24 hours to four weeks, from about 24 hours to six weeks, from about 24 hours to eight weeks, from about 24 hours to ten weeks, from about 24 hours to twelve weeks, etc. In some embodiments, trospium is administered to the bladder for about 42 days. In some embodiments, trospium is administered to the bladder for about 56 days or 112 days.

In some embodiments, average total daily urinary recovery of trospium during the device indwelling time is at least about 0.1, 0.5, 1, 1.5, 2, 2.5, or 3 mg/day. In some embodiments, average total daily urinary recovery of trospium during the device indwelling time is no more about 30, 18, 15, 12, 10, 9, or 8 mg/day. In some embodiments, average total daily urinary recovery of trospium during the device indwelling time is about 0.1 mg/day to about 30 mg/day, about 1 mg/day to about 25 mg/day, about 2 mg/day to about 10 mg/day, about 3 mg/day to about 9 mg/day.

Patient Populations

The individuals treated with the methods described herein can be a mammal. In some embodiments, the individual is human.

In some embodiments, the individual has idiopathic overactive bladder.

In some embodiments, the individual has received a previous therapy for overactive bladder. In some embodiments, the individual is refractory to the previous therapy. In some embodiments, the individual has recalcitrant overactive bladder. In some embodiments, the individual has severe overactive bladder. In some embodiments, the individual does not respond to the previous therapy. In some embodiments, the individual progresses on the previous therapy. In some embodiments, the individual has a recurrence of baseline symptoms upon the completion of the prior therapy, for example, wherein the individual has at least an about 10%, 20%, 30%, 40%, 50%, 60%, 70%, 80%, or 90% recurrence in baseline symptoms. In some embodiments, the prior therapy is an oral therapy. In some embodiments, the prior therapy is a local therapy. In some embodiments, the prior therapy comprises administering an antimuscarinic agent. In some embodiments, the agent is selected from the group consisting of Botox®, VESIcare® (solifenacin succinate) and Detrol® LA (tolterodine tartrate). In some embodiments, the prior therapy comprises administering an anticholinergic agent.

In some embodiments, the individual has not received a previous therapy for overactive bladder.

In some embodiments, the individual is not eligible for an oral therapy. For example, the individual cannot tolerate side effects from the therapy. In some embodiments, the individual is old or frail. In some embodiments, the oral therapy comprises an anticholinergic agent. In some embodiments, the oral therapy comprises an antimuscarinic agent. In some embodiments, the agent is selected from the group consisting of Botox®, VESIcare® (solifenacin succinate) and Detrol® LA (tolterodine tartrate).

In some embodiments, the individual has a neurological condition. In some embodiments, the neurological condition is multiple sclerosis. In some embodiment, the neurological condition is Parkinson's disease. In some embodiments, the neurological condition is Alzheimer's disease. In some embodiments, the individual has had a stroke.

In some embodiments, the individual has symptoms of overactive bladder with a predominant urge component, for example, wherein more than 50% of the symptoms of overactive bladder are associated with urgency (as opposed to frequency). In some embodiments, the individual has symptoms of overactive bladder with a predominant urge component for at least about 1, 2, 3, 4, 5, 6, 7, 8, 9, 10, 11, or 12 weeks. In some embodiments, the individual has symptoms of overactive bladder with a predominant urge component for at least about 3, 4, 5, 6, 7, 8, 9, 10, 11, or 12 months. In some embodiments, the individual has about four, five, six, seven, eight or more voids per 24 hours. In some embodiments, the individual has at least about 2, 3, 4, 5, or 6 incontinence episodes associated with urgency in a 3-day diary. In some embodiments, the individual has at least one, two or three episodes that occur each 24 hours or per day.

In some embodiments, the individual has urinary incontinence or urge incontinence.

In some embodiments, the individual has a post-void residual volume (PVR) of less than about 300 mL (such as less than about 300 mL, 250 mL, 200 mL, 150 mL, or 100 mL).

In some embodiments, the individual is a female. In some embodiments, the individual is a male.

In some embodiments, the individual is about 40 to about 70 years old. In some embodiments, the individual is at least about 40, 45, 50, 55, 60, 65, or 70 years old. In some embodiments, the individual is no more than about 70, 65, 60, 55, 50, 45, or 40 years old.

Overactive Bladder

In some embodiments, the overactive bladder is associated with a neurological condition. In some embodiments, the neurological condition is multiple sclerosis. In some embodiment, the neurological condition is Parkinson's disease. In some embodiments, the neurological condition is Alzheimer's disease. In some embodiments, the neurological condition is a previous stroke.

In some embodiments, the overactive bladder is not associated with a neurological condition.

Endpoints

In some embodiments, the methods provided herein prolong symptom relief for an individual having overactive bladder, comprising delivering trospium locally to the bladder for at least about 24 hours. In some embodiments, the individual experience at least about 10%, 20%, 30%, 40%, 50%, 60%, 70%, 80%, or 90% of baseline symptom relief during or after the completion of the administration of trospium. In some embodiments, symptom relief comprises a reduction in urgency and/or frequency. In some embodiments, symptom relief comprises a reduction in an aberrant urge. In some embodiments, urgency and/or frequency is reduced by at least about 10%, 20%, 30%, 40%, 50%, 60%, 70%, 80%, or 90% from baseline during or after the completion of the administration of trospium. In some embodiments, the symptom relief comprises a reduction in urinary incontinence and/or urge incontinence (e.g., daily incontinence episodes or incontinence episodes within 3 days). In some embodiments, urinary incontinence and/or urge incontinence (e.g., daily incontinence episodes or incontinence episodes within 3 days) is reduced by at least about 10%, 20%, 30%, 40%, 50%, 60%, 70%, 80%, or 90% from baseline symptom during or after the completion of the administration of trospium. In some embodiments, the symptom relief is prolonged for at least about 1, 2, 3, 4, 5, 6, or 7 days after the completion of the administration of trospium. In some embodiments, the symptom relief is prolonged for at least about 1, 2, 3, 4, 5, 6, 7, 8, 9, 10, 11, or 12 weeks after the completion of the administration of trospium. In some embodiments, the symptom relief is prolonged for at least about 3, 4, 5, 6, 7, 8, 9, 10, 11, or 12 months after the completion of the administration of trospium.

In some embodiments, the individual has a reduction in daily micturition episodes during or after the completion of the administration of trospium. In some embodiments, daily micturition episodes are reduced by at least about 2.5%, 5%, 7.5%, or 10% from baseline symptom during or after the completion of the administration of trospium. In some embodiments, the reduction is prolonged for at least about 1, 2, 3, 4, 5, 6, or 7 days after the completion of the administration of trospium. In some embodiments, the reduction is prolonged for at least about 1, 2, 3, 4, 5, 6, 7, 8, 9, 10, 11, or 12 weeks after the completion of the administration of trospium. In some embodiments, the reduction is prolonged for at least about 3, 4, 5, 6, 7, 8, 9, 10, 11, or 12 months after the completion of the administration of trospium.

In some embodiments, the individual has an increase in voided volume per micturition during or after the completion of the administration of trospium. In some embodiments, the increase in voided volume per micturition is at least about 2.5%, 5%, 7.5%, 10%, 20%, 25%, 30%, 35%, or 40% from baseline symptom during or after the completion of the administration of trospium. In some embodiments, the increase is prolonged for at least about 1, 2, 3, 4, 5, 6, or 7 days after the completion of the administration of trospium. In some embodiments, the increase is prolonged for at least about 1, 2, 3, 4, 5, 6, 7, 8, 9, 10, 11, or 12 weeks after the completion of the administration of trospium. In some embodiments, the increase is prolonged for at least about 3, 4, 5, 6, 7, 8, 9, 10, 11, or 12 months after the completion of the administration of trospium.

In some embodiments, provided herein is a method for improving the quality of life of an individual comprising administering an effective amount of trospium locally to the bladder for at least about 24 hours. In some embodiments, the quality of life score of the individual is increased. In some embodiments, the individual has an improved quality of life score at least about 24 hours after the local administration of trospium is completed compared with prior the quality of life score prior to local treatment with trospium. In some embodiments, the quality of life score includes a score based upon the frequency with which the individual has experienced one or more events over a period of time, for example, none of the time, a little of time, some of the time, a good bit of the time, most of the time, and all of the time. In some embodiments, the event comprises being bothered by a sudden urge to urinate with little or no warning. In some embodiments, the event comprises being bothered by an accidental loss of small amounts of urine. In some embodiments, the event comprises being bothered by nighttime urination. In some embodiments, the event comprises being bothered by waking up at night because he/she had to urinate. In some embodiments, the event comprises being bothered urine loss associated with a strong desire to urinate. In some embodiments, the quality of life score of the individual is improved by about 10%, 20%, 30%, 40%, 50%, 60% 70% or 80% after local administration of trospium. In some embodiments, the quality of life score of the individual is improved for at least 1, at least 2, at least 3, at least 4, at least 5, at least 6, at least 7, at least 8, at least 10, at least 11, or at least 12 weeks after local trospium administration is completed.

In some embodiments, provided herein is a method for improving the quality of life score of an individual comprising administering an effective amount of trospium locally to the bladder for at least about 24 hours. In some embodiments, the individual has an improved quality of life score at least about 24 hours after the local administration of trospium is completed compared with prior the quality of life score prior to local treatment with trospium. In some embodiments, the quality of life score includes a score based upon the frequency with which the individual has experienced one or more events over a period of time, for example, none of the time, a little of time, some of the time, a good bit of the time, most of the time, and all of the time. In some embodiments, the event comprises being bothered by a sudden urge to urinate with little or no warning. In some embodiments, the event comprises being bothered by an accidental loss of small amounts of urine. In some embodiments, the event comprises being bothered by nighttime urination. In some embodiments, the event comprises being bothered by waking up at night because he/she had to urinate. In some embodiments, the event comprises being bothered urine loss associated with a strong desire to urinate. In some embodiments, the quality of life score of the individual is improved by about 10%, 20%, 30%, 40%, 50%, 60% 70% or 80% after local administration of trospium. In some embodiments, the quality of life score of the individual is improved for at least 1, at least 2, at least 3, at least 4, at least 5, at least 6, at least 7, at least 8, at least 10, at least 11, or at least 12 weeks after local trospium administration is completed.

In some embodiments, provided herein is a method of reducing the bother associated with bladders symptoms in an individual comprising delivering trospium to the bladder of an individual for at least about 24 hours. In some embodiments, the bother score of the individual is reduced. In some embodiments, the bother score is reduced at least about 24 hours after the local administration of trospium is completed compared with prior to local treatment with trospium. n some embodiments, the quality of life score can include a score based upon the frequency with which the individual has experienced one or more events over a period of time, for example, none of time, a little of time, some of the time, a good bit of the time, most of the time, and all of the time. In some embodiments, the event comprises planning escape routes to restrooms in public places. In some embodiments, the event comprises bladder symptoms affecting the frequency at which the individual's bladder symptoms make the individual feel like there is something wrong with him/her. In some embodiments, the event comprises bladder symptoms interfering with his/her ability to get a good night's rest. In some embodiments, the event comprises bladder symptoms that make the individual frustrated or annoyed about the amount of time he/she spent in the restroom. In some embodiments, the event comprises bladder symptoms that make the individual avoid activities away from restrooms (e.g., walking, running, hiking). In some embodiments, the event comprises bladder symptoms that awaken the individual during sleep. In some embodiments, the event comprises bladder symptoms that cause the individual to decrease his or her physical activities (exercising, sports, etc.). In some embodiments, the event comprises a bladder symptoms that cause the individual to have problems with his/her partner or spouse. In some embodiments, the event comprises bladder symptoms that make the individual uncomfortable while traveling with others because of needing to stop for a restroom. In some embodiments, the event comprises bladder symptoms that affect the individual's relationships with family and friends. In some embodiments, the event comprises embarrassment caused by the individual's bladder symptoms. In some embodiments, the event comprises when the individual's bladder symptoms cause the individual to locate the closest restroom upon arrival at a new place. In some embodiments, the bother score of the individual is improved by about 10%, 20%, 30%, 40%, 50%, 60% 70% or 80% after local administration of trospium. In some embodiments, the bother score of the individual is improved for at least 1, at least 2, at least 3, at least 4, at least 5, at least 6, at least 7, at least 8, at least 10, at least 11, or at least 12 weeks after local trospium administration is completed.

In some embodiments, the quality of life score [i.e., health-related quality of life (HRQL) transformed score] and the bother score (i.e. symptom severity transformed score) are calculated from subject's self-evaluations via a questionnaire. Exemplary questionnaires are shown in FIGS. 13-14. Evaluations can be made prior to (such as immediately prior to) the trospium administration to establish a baseline. Evaluations can also be made at different time points during or after the administration of trospium.

For example, the quality of life score can be calculated from FIG. 14 raw score as follows, where the raw score was the total score from the values of items 1-13. Quality of life score=(Highest possible score−Actual raw score)/Possible raw score range×100 where the highest possible score was 78 and the possible raw score range was 65. Note that higher quality of life score values are indicative of better quality of life.

The bother score can be calculated from FIG. 13 raw score as follows, where the raw score was the total score from the values of items 1-6. Bother score=(Actual raw score−lowest possible raw score)/Possible raw score range× 100, where the lowest possible raw score=6, and the possible raw score range was 30. Note that higher bother score values are indicative of greater symptom severity or bother and lower scores indicate minimal symptom severity.

In some embodiments, the trospium is delivered via an intravesical device described herein. In some embodiments, the individual has a high tolerability to the device (for example, less than about 30%, 20%, 15%, 10%, 5% or 2% of the individuals require removal of the device prior to the completion of the scheduled treatment.

In some embodiments, the method does not cause a significant level of adverse events in the individual. Exemplary adverse events include urinary tract infection (UTI), bladder pain, hematuria, sinusitis and bladder discomfort. In some embodiments, less than about 50%, 40%, 30%, 25%, or 20% of the individuals develop an UTI during the treatment period. In some embodiments, less than about 50%, 40%, 30%, 25%, or 20% of the individuals develop bladder pain during the treatment period. In some embodiments, less than about 50%, 40%, 30%, 25%, or 20% of the individuals develop hematuria during the treatment period. In some embodiments, less than about 50%, 40%, 30%, 25%, or 20% of the individuals develop sinusitis during the treatment period. In some embodiments, less than about 50%, 40%, 30%, 25%, or 20% of the individuals develop bladder discomfort during the treatment period.

In some embodiments, the bladder post-void residual volume (PVR) in the individual is reduced by at least about 5%, 10%, 15%, 20%, 25%, 30%, 35%, or 40% after the administration of trospium. In some embodiments, the reduction is observed within about 7 days, 21 days or 35 days after administration of trospium.

Delivery

I. Intravesical Devices a. Device Shape

In some embodiments, the methods provided herein comprise locally delivering to the bladder an effective amount of trospium using an intravesical device. In some embodiments, the intravesical device comprises a deployment shape and a retention shape. For example, the device may be elastically deformable between a relatively straightened or uncoiled shape suited for insertion through a lumen (e.g., the urethra) into the bladder of the individual (the deployment shape) and a retention shape suited to retain the device within the bladder. For the purposes of this disclosure, terms such as "relatively expanded shape," "relatively higher-profile shape," or "retention shape" generally denote any shape suited for retaining the device in the intended implantation location, including but not limited to a pretzel shape or other coiled shape (e.g., comprising bi-oval or overlapping coils) that is suited for retaining the device in the bladder. The retention shape provides that the device resists becoming entrained in urine and excreted when the individual voids. Similarly, terms such as "relatively lower-profile shape" or "deployment shape" generally denote any shape suited for deploying the drug delivery device into the body, for example the bladder, including, but not limited to, including a linear or elongated shape that is suited for deploying the device through the working channel of catheter, cystoscope, or other deployment instrument positioned in the urethra or in the bladder, for example, a suprapubic cystostomy or suprapubic catheter (also known as a vesicostomy or epicystostomy) used to drain urine from the bladder in individuals with obstruction of normal urinary flow. In embodiments, the drug delivery device may naturally assume the relatively expanded shape and may be deformed, either manually or with the aid of an external apparatus, into the relatively lower-profile shape for insertion into the body. For example, the external apparatus may be an inserter configured for transurethral insertion. Once deployed the intravesical device may spontaneously or naturally return to the initial, relatively expanded shape for retention in the body. In some embodiments, the device behaves like a spring, deforming in response to a compressive load (e.g., deforming the device into a deployment shape) but spontaneously returning to a retention shape once the load is removed.

In some embodiments, the shape changing functionality of the intravesical device described in the preceding paragraph may be provided by including a shape retention frame (i.e., a "retention frame") in the device, such as those disclosed in published applications US2012/0203203, US2013/0158675, US2015/0360012, US20150165177, US2015/0165178, US20160199544, WO2014/145638, WO2015200752, and WO2011/031855, which are incorporated herein by reference. In some embodiments, the device may include a retention frame lumen in which the retention frame, which may be an elastic wire, e.g., a superelastic alloy such as nitinol, is secured. The retention frame may be configured to return spontaneously to a retention shape, such as a "pretzel" shape or another coiled shape, such as those disclosed in the applications previously incorporated. In particular, the retention frame may retain the device in the body, such as in the bladder. The retention shape provides that the device resists becoming entrained in urine and excreted when the individual voids. For example, the retention frame may have an elastic limit and modulus that allows the device to be introduced into the body in a relatively lower-profile shape, permits the device to return to the relatively expanded shape once inside the body, and impedes the device from assuming the relatively lower-profile shape within the body in response to expected forces, such as the hydrodynamic forces associated with contraction of the detrusor muscle and urination. Thus, the device may be retained in the individual's bladder once deployed, limiting or preventing accidental expulsion.

In some other embodiments, the shape changing functionality of the intravesical device may be provided by forming the device housing at least in part of a thermally shape set elastic polymer, for example, as described in WO 2016/172704.

The material used to form the device body (i.e., the housing), at least in part, may be elastic or flexible to permit moving the device between deployment and retention shapes. When the device is in the retention shape, the retention frame portion may tend to lie inside the drug reservoir portion, although the retention frame portion can be positioned inside, outside, above, or below the drug reservoir portion in other cases. The material used to form the device body may be water permeable so that solubilizing fluid (e.g., urine) can enter the drug reservoir portion to solubilize the non-liquid forms of trospium, chemotherapeutic agent, immunomodulating agent, additional therapeutic agent, functional agent, or combination thereof contained in the drug reservoir once the device is deployed into the bladder. For example, silicone or another biocompatible elastomeric material may be used. In other embodiments, the device body may be formed, at least in part, of a water-impermeable material.

In some embodiments, the device body is made of an elastic, biocompatible polymeric material. The material may be non-resorbable or resorbable. Example non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, and poly(siloxanes). Example resorbable materials, specifically biodegradable or bioerodible polymers, include synthetic polymers selected from poly(amides), poly(esters), poly (ester amides), poly(anhydrides), poly(orthoesters), polyphosphazenes, pseudo poly(amino acids), poly(glycerol-sebacate), poly(lactic acids), poly(glycolic acids), poly(lactic-co-glycolic acids), poly(caprolactones), poly(caprolactone) (PC) derivatives, amino alcohol-based poly(ester amides) (PEA) and poly(octane-diol citrate) (POC), and other curable bioresorbable elastomers. PC-based polymers may require additional cross-linking agents such as lysine diisocyanate or 2,2-bis(e-caprolacton-4-yl)propane to obtain elastomeric properties. Copolymers, mixtures, and combinations of the above materials also may be employed.

In some embodiments, the device body comprises silicone, thermoplastic polyurethane, ethyl vinyl acetate (EVA), or a combination thereof. In some embodiments, the device body comprises two different thermoplastic materials, one of which is a hydrophilic thermoplastic polyurethane and is drug permeable, with the other being drug-impermeable. The drug impermeable material may be a selected from the group consisting of hydrophilic polyurethane, hydrophilic polyesters, and hydrophilic polyamides. The device body may comprise an annular tube formed by an extrusion or coextrusion process, using one or more these materials, as described in U.S. Publication 2016/0310715, which is incorporated herein by reference.

b. Drug Core/Payload

In embodiments in which trospium is delivered from an intravesical drug delivery device, the composition may be housed in the device in various forms, which may depend on the particular mechanism by which the device controllably releases the composition into fluid (e.g., urine) in the bladder. In some embodiments, the composition is provided in a solid, semi-solid, or other non-liquid form, which advantageously may facilitate stable storage of the composition before the device is used and advantageously may enable the composition payload of the device to be stored in smaller volume than would be possible if the composition were housed in the form of a liquid solution. In some embodiments, the non-liquid form is selected from tablets, granules, pellets, powders, semisolids (e.g., an ointment, cream, paste, or gel), capsules, and combinations thereof. In one embodiment, the composition is in the form of a plurality of tablets, such as mini-tablets described in U.S. Pat. No. 9,757,546.

For example, trospium, may take such forms as suspensions, solutions, colloids, micelles, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In one embodiment, trospium is formulated with one or more excipients that include a viscosity enhancing agent to control release of trospium from a release aperture in the device housing. In another embodiment, the device reservoir includes both trospium and a viscosity enhancing agent, but they are not co-formulated and instead are provide in discrete regions within the reservoir, e.g., as separate tablets. Suitable viscosity enhancing agents, including but not limited to polyethylene oxide (PEO), are known in the pharmaceutical arts. In some variations of the embodiment, the viscosity enhancing agent may be provided, e.g., formulated, with urea or another osmotic agent.

In one embodiment, trospium is delivered to the bladder of the individual with a solubility enhancing agent. In an embodiment, the solubility enhancing agent is urea. In one embodiment, the urea is provided in a tablet or other solid form and loaded with trospium in the drug reservoir of an intravesical drug delivery device. The urea may also function, depending on the device, as an osmotic agent to facilitate generation of an osmotic pressure in a drug reservoir. In a particular embodiment, trospium and the osmotic agent are configured as separate payloads (i.e., powders, tablets, or other solid forms) positioned within different regions of the drug reservoir as described in PCT WO 2015/026813 (Lee et al.) which is incorporated by reference herein.

In some embodiments, the device may comprise a drug reservoir lumen. In some of these embodiments, each drug reservoir lumen may hold one or several drug tablets or other solid drug units. In one embodiment, the device holds from about 10 to 100 cylindrical drug tablets, such as mini-tablets, among a number of discrete drug reservoir lumens. In certain embodiments, the mini-tablets may each have a diameter of about 1.0 to about 3.3 mm, such as about 1.5 to about 3.1 mm, and a length of about 1.5 to about 4.7 mm, such as about 2.0 to about 4.5 mm. In some other embodiments, the drug reservoir lumen contains a powder form or granulated form of trospium.

In some embodiments, the intravesical device contains and releases a functional agent along with trospium. The functional agent may facilitate release of the drug from the device and/or may facilitate stabilization (i.e. retardation of degradation) of trospium in urine in the bladder. For example, the functional agent may include an anti-protease if proteolytic degradation of trospium in urine is a concern.

c. Drug Housing

The release of trospium from the intravesical devices described herein may be driven and controlled by different mechanisms of action. In various embodiments, the drug may be released from the intravesical drug delivery device by diffusion through a wall of the drug housing, by diffusion through one or more defined apertures in a wall of the drug housing, by osmotic pressure through an aperture in the drug housing, by osmotic pressure through one or more transiently formed microchannels, by erosion of a drug formulation in contact with urine in the bladder, or by a combination thereof. In some embodiments, drug release is controlled by drug diffusion through/from a drug-permeable polymer or matrix component defining part of the device housing. In one embodiment, the device includes a drug-permeable polymer component.

The size of the housing, including the thickness of the wall, may be selected based on the volume of drug (and functional agent, if any) formulation(s) to be contained, the desired rate of delivery of the drug from the device body/housing, the intended site of implantation of the device within the body, the desired mechanical integrity for the device, the desired release rate or permeability to water and urine, the desired induction time before onset of initial release, and the desired method or route of insertion into the body, among other factors. In embodiments in which the housing is a tube, the tube wall thickness may be determined based on the mechanical properties and water permeability of the tube material, as a tube wall that is too thin may not have sufficient mechanical integrity while a tube wall that is too thick may experience an undesirably long induction time for initial drug release from the device and/or may not have sufficient flexibility to permit delivery through a urethra or other narrow body lumen.

In some embodiments, the housing may include an elongated, annular tube having an inner diameter from about 2 mm to about 5 mm. The drug, and functional agent if any, may be solid tablets having a diameter substantially the same as the inner diameter of the elongated annular tube. In some embodiments, the housing holds one or more first units (e.g., tablets) comprising a drug and one or more second units (e.g., tablets) comprising a functional agent which facilitates release of the drug and/or which facilitates stabilization of trospium in urine in the bladder. One or more of the first unit tablets may fill a length from about 1 cm to about 3 cm of the lumen of the tube, and one or more of the second unit tablets may fill a length from about 10 cm to about 15 cm of the lumen of the tube. In one embodiment, the ratio of volume of the first unit(s) to volume of the second unit(s) is from about 0.05 to about 0.5. Other lengths and ratios of the tablet payloads are envisioned.

In some embodiments, the housing may be an elongated, annular tube having a wall thickness from 0.1 to 0.4 mm, such as a wall thickness of 0.2 mm. The housing material may comprise one or more biocompatible elastomers. The housing material may be selected such that the housing has a durometer from 25 A to 80 A, such as 25 A, 50 A, 65 A, 70 A, or 80 A.

In various embodiments, the intravesical device may release the drug continuously or intermittently to achieve a concentration of the drug in the bladder that produces a sustained, therapeutically effective concentration of the drug in urine in the bladder as described in the methods provided herein. In certain embodiments, the intravesical device may release trospium in an amount of from 1 mg/day to 1000 mg/day, for example from 20 mg/day to 300 mg/day or from 25 mg/day to 300 mg/day. In certain embodiments, these release rates are provided over a treatment period as described herein. In certain embodiments, these release rates are provided over a treatment period from 14 days to 21 days.

d. Osmotic and Diffusion Systems

Following in vivo deployment, the device releases trospium. Release may occur, as described above, due to an osmotic pressure gradient between the interior and exterior of the device, the drug passing through one or more orifices or passing pores in the device under the force of osmotic pressure. Release may also occur by diffusion, whereby the drug passes through one or more orifices or passing pores in the device and/or through a drug-permeable wall of the device, due to a drug concentration gradient between the interior and exterior of the device. Combinations of these release modes within a single device are possible, and in some embodiments are preferred in order to achieve an overall drug release profile not readily achievable from either mode individual.

In some embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. This "dissolved drug" may include micro- and nanoscale particulates of the drug in suspension that remain following substantial dissolution of the solid form of the drug and are also able to be released from the device, e.g., through an aperture in the device housing. For example, the drug may be solubilized upon contact with urine in the bladder. In certain embodiments, a water permeable wall portion of the housing is permeable to the drug in aqueous solution, such that solubilized drug is released via the wall portion, also referred to herein as "trans-wall diffusion." After the device is deployed in the individual's bladder, urine permeates through the wall, enters the reservoir, and solubilizes trospium, and the functional agent if present. In some embodiments, the drug then diffuses directly through the wall at a controlled rate, due to a drug concentration gradient between the interior and the exterior of the device. For example, the housing and/or any water or drug permeable wall portions may be silicone, a thermoplastic polyurethane, ethylene-co-vinyl acetate (EVA), or a combination thereof.

In some embodiments, the intravesical device includes (i) a body that comprises a wall bounding a reservoir defined within the body, wherein the wall has a preformed through-hole, and comprises a water-permeable portion, and the body includes an elastic portion; (ii) a drug formulation, which comprises a trospium, disposed within the reservoir; and (iii) a restraining plug closing off an opening of the body and contacting the elastic portion of the body, wherein the opening is in fluid communication with the reservoir, wherein the water-permeable portion of the wall is configured to permit water to enter the device and contact the drug formulation in the reservoir, and wherein release of the trospium from the device is controlled by (a) release of the trospium through the preformed through-hole in the wall, and (b) release of the trospium through the transient formation of one or more microchannels between the elastic portion of the body and the restraining plug, extending to the opening, upon the generation within the reservoir of a hydrostatic pressure effective to form the one or more microchannels. The drug formulation may be in the form of plurality of tablets, and the body may be in the form of a silicone tube. These embodiments are further described in PCT/US18/16463, which is incorporated herein by reference.

Figure 2:
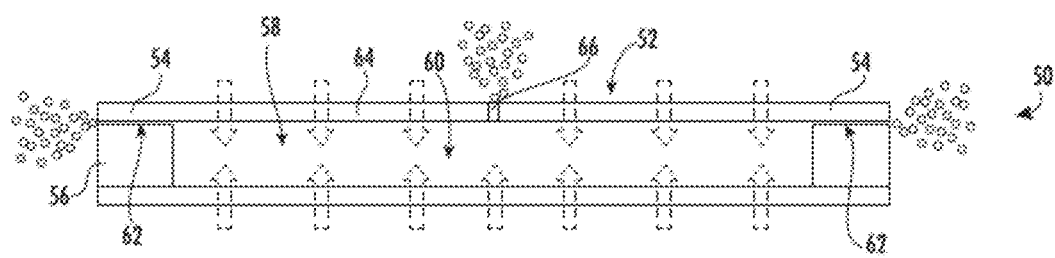
FIG. 2 is a cross-sectional side view of one embodiment of a device having a preformed sidewall orifice and two restraining end plugs.
Figure 3B:
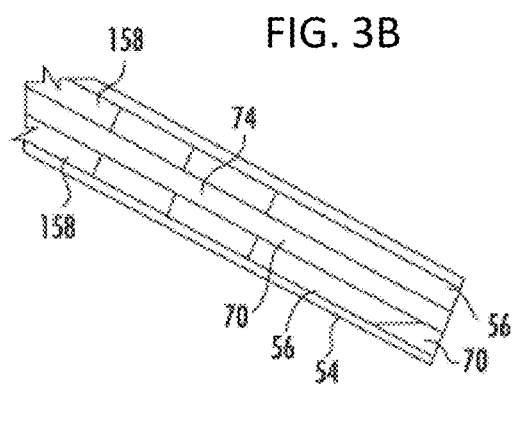
FIG. 3B is a cross-sectional magnified view of one of the end plugs of FIG. 3A.
Figure 3A:
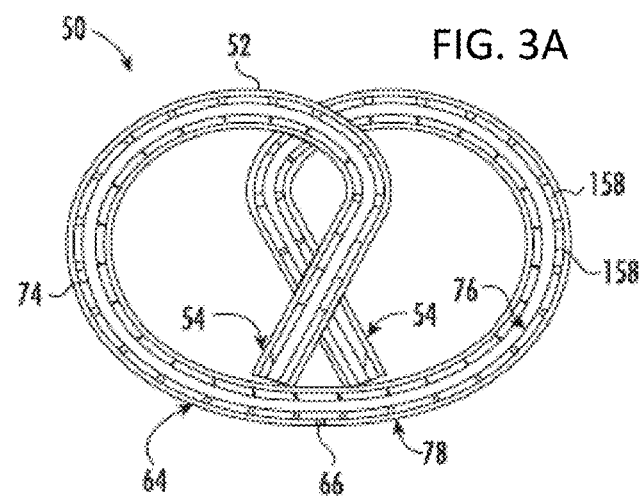
FIG. 3A is a plan view of one embodiment of a device having a preformed sidewall orifice and two restraining end plugs.
Figure 3C:
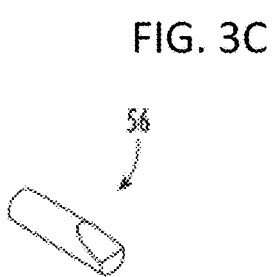
FIG. 3C is an exploded perspective view of the end plug of FIG. 3B.
Figure 4:
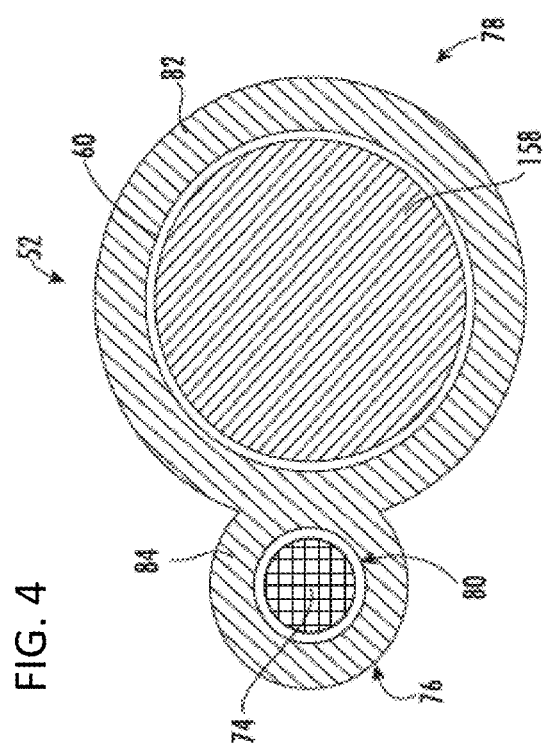
FIG. 4 is a cross-sectional end view of one embodiment of a drug delivery device.

In a first aspect, as shown in FIGS. 1A-1D, the drug delivery devices 50 described herein include one or more restraining plugs 56 in contact with the elastic portion(s) 54 of the device body 52, to permit drug release via the distal opening(s) of the device body, as described in U.S. Patent Application Publication 2016/0008271 to Lee, which is incorporated by reference herein in relevant part. However, in contrast to the no-orifice (i.e., no predefined aperture system) of U.S. Patent Application Publication 2016/0008271 to Lee, in certain embodiments, as shown in FIGS. 2 and 3A, the devices include at least one preformed through-hole (i.e., orifice) 66 disposed in a wall of the device body 52.

Thus, in certain embodiments, as shown in FIGS. 1-4, a drug delivery device 50 includes a body 52 that has a wall bounding a reservoir 60 defined within the body 52, the wall having at least one preformed through-hole 66 disposed therein and including a water-permeable portion 64, the body 52 including an elastic portion 54; a drug formulation 58 which contains a drug, the drug formulation 58 being disposed within the reservoir 60; and at least one restraining plug 56 closing off an opening of the body 52 and contacting the elastic portion 54 of the body 52, the opening being in fluid communication with the reservoir 60. The water-permeable portion 64 of the wall is configured to permit water to enter the drug delivery device 50 and contact the drug formulation 58 located in the reservoir 60 and release of the drug 58 from the device 50 is controlled by at least one of (i) release of the drug 58 through the at least one preformed through-hole 66 (i.e., aperture, orifice) in the wall, and (ii) release of the drug through the transient formation of one or more microchannels 62 between the elastic portion 54 of the body 52 and the at least one restraining plug 56, extending to the opening, upon the generation of a hydrostatic pressure effective to form the one or more microchannels 62. In these embodiments, the restraining plugs 56 may be partially or wholly unsealed at the distal end openings of the device 50. Such systems have been found to provide consistent and reproducible drug release profiles, while providing a relief valve system that beneficially provides release of the drug when the through-hole is partially or fully clogged. Thus, the device may operate to release drug via the preformed orifice unless and until the hydrostatic pressure within the drug reservoir reaches a threshold pressure of the restraining plug(s), at which point release via the restraining plugs occurs. For example, release of the drug through the at least one preformed through-hole may be osmotically driven.

Figure 5A:
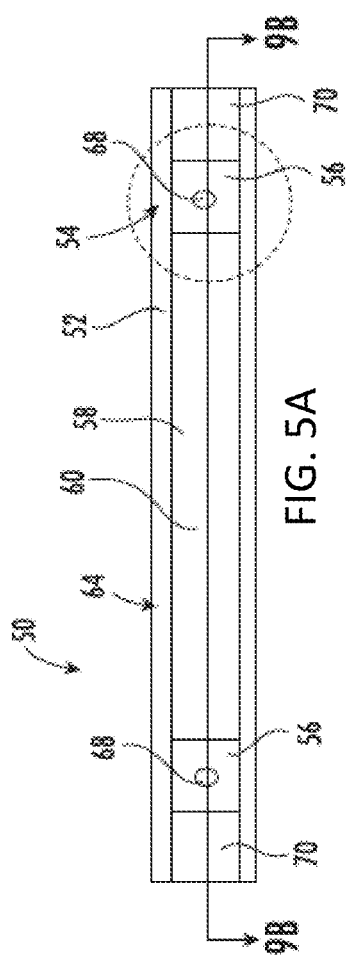
FIG. 5A is a plan view of one embodiment of a drug delivery device having restraining plugs and a preformed release port.
Figure 5B:
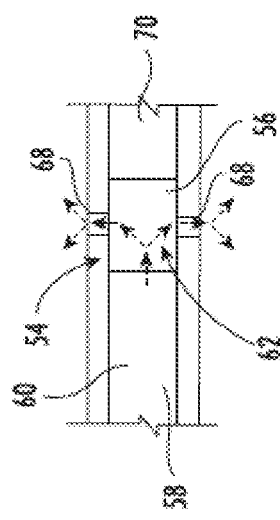
FIG. 5B is an enlarged cross-sectional view of the device of FIG. 5A.
Figure 6A:
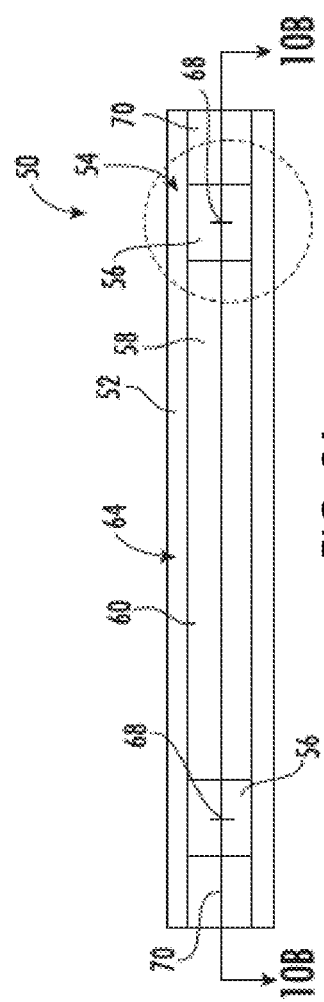
FIG. 6A is a plan view of one embodiment of a drug delivery device having restraining plugs and a preformed release port.
Figure 9A:
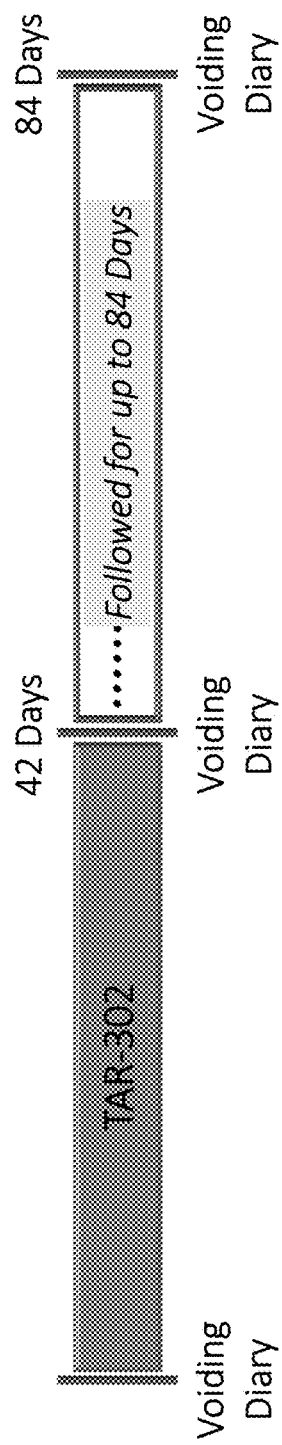
FIG. 9A and FIG. 9B show the scheme of the study (FIG. 9A) and average daily incontinence episodes assessed at Day 0 (baseline), Day 42 and Day 84 after the insertion of TAR-302 (FIG. 9B).
Figure 9B:
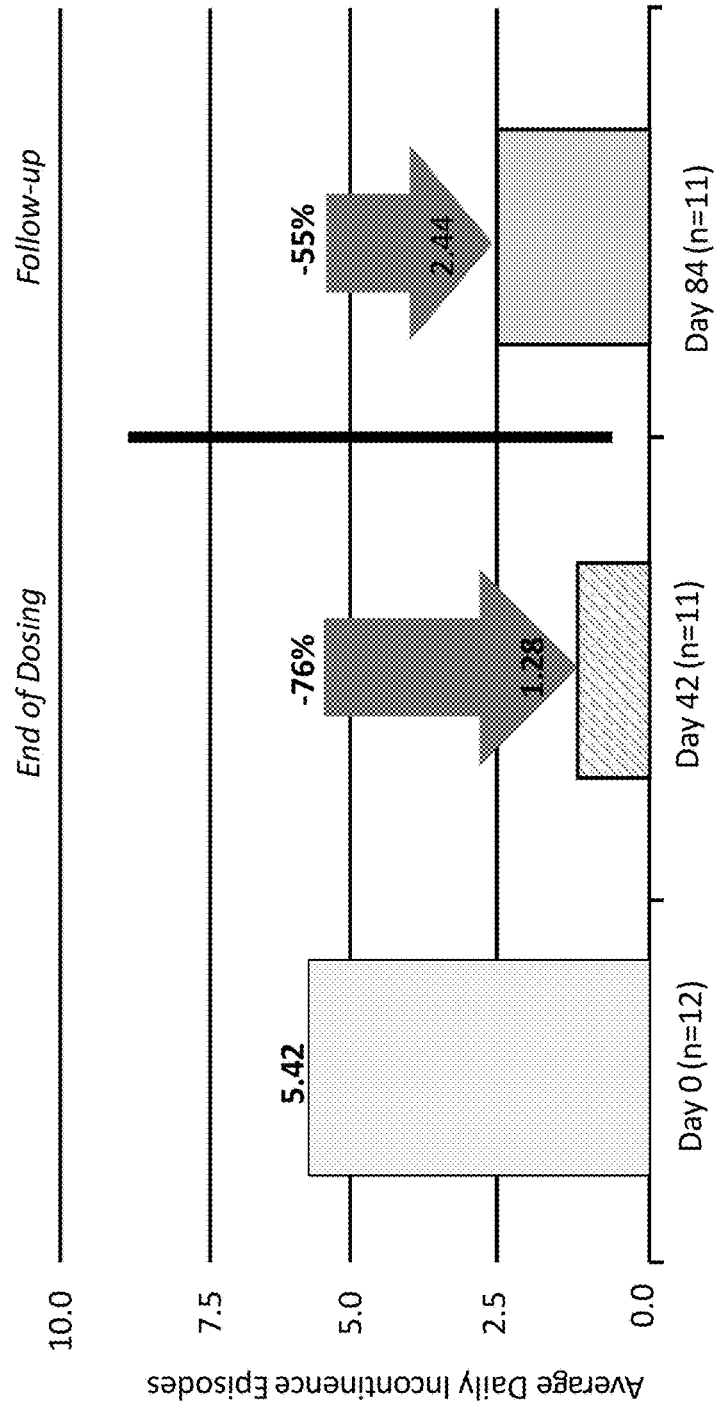

In a second aspect, as shown in FIGS. 5-6, the drug delivery devices 50 described herein include sealed distal ends (shown sealed with adhesive 70), with one or more restraining plugs 56 in contact with the elastic portion(s) 54 of the device body 52, to permit drug release via preformed release port(s) 68 in the device body 52 (e.g., sidewall) adjacent the restraining plug 56. The elastic portions 54 may be at or near the ends of the device 50 (as shown in FIGS. 9-10), or may be otherwise disposed along the length of the device, such as at or near the center of the device. The retraining plug(s) 56 may be situated adjacent the one or more preformed release port(s) 68 in the device body 52, such that the restraining plug(s) 56 cover, and effectively close, the preformed release port(s) 68 when the threshold hydrostatic pressure within the drug reservoir 60 has not been reached. In such embodiments, the restraining plugs 56 and elastic portions 54 of the device may be similar to those described above and in U.S. Patent Application Publication 2016/0008271 to Lee, except that the one or more microchannels 62 transiently formed upon the drug reservoir 60 reaching a threshold hydrostatic pressure extend from the drug reservoir 60 to the preformed release port(s) 68.

Thus, in certain embodiments, as shown in FIGS. 5-6, a drug delivery device 50 includes a tubular body 52 that comprises a wall bounding a reservoir 60 defined within the body, the wall having a water-permeable portion 64 and an elastic portion 54 having at least one preformed release port 68 (e.g., through-hole, aperture, orifice, slit) disposed therein; a drug formulation 58 which contains a drug, the drug formulation 58 being disposed within the reservoir 60, wherein the water-permeable portion 64 of the wall permits water to enter the drug delivery device and contact the drug formulation 58 located in the reservoir 60; and at least one restraining plug 56 secured within the reservoir 60 in contact with the elastic portion 54 of the body 52 and adjacent the at least one preformed release port 68, such that the at least one restraining plug 56 controls release of the drug from the device, via the at least one preformed release port 68, by the transient formation of one or more microchannels 62 between the elastic portion 54 of the body and the at least one restraining plug 56, extending to the at least one preformed release port 68, upon the generation of a hydrostatic pressure within the reservoir 60 effective to form the one or more microchannels 62. In certain of these embodiments, the at least one preformed release port 68 is a through-hole or a slit disposed in the wall of the body 52.

Figure 6B:
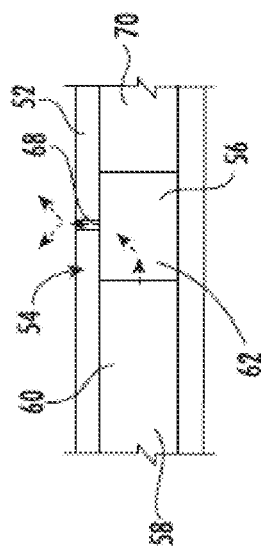
FIG. 6B is an enlarged cross-sectional view of the device of FIG. 6A.

Any suitable number and location of restraining plugs 56 and preformed release ports 68 may be used, to achieve the desired drug release profile. For example, as shown in FIG. 5B, the device 50 may include two preformed ports 68, here shown as apertures, spaced 180 degrees from one another in a tubular device body 52, such that a single restraining plug 56 is positioned adjacent both apertures. As shown in FIG. 5B, a pair of apertures 68 and a corresponding restraining plug 56 may be provided at or near each distal end of the device. For example, as shown in FIG. 6B, a single preformed port 68, here shown as a slit, may be disposed adjacent each restraining plug 56. As shown in FIG. 6B, a preformed port 68 and a corresponding restraining plug 56 may be provided at or near each distal end of the device.

In some embodiments, the drug delivery device includes a permeation system as described in WO2014/145638 and U.S. Publication 2016/0310715, which are herein both incorporated by reference in its entirety. In some embodiments, the drug delivery device includes a housing having a closed drug reservoir lumen bounded by a first wall structure and a hydrophilic second wall structure; and a drug formulation comprising trospium contained in the drug reservoir lumen, wherein the first wall structure is permeable or impermeable to water and impermeable to the drug, and the second wall structure is permeable to trospium.

In some embodiments, the device housing has walls bounding and defining the drug reservoir of the device that are made of a first material that serves as the first wall structure and a second material that serves as the second wall structure, such that drug release occurs essentially only through the second material. In one embodiment, the device does not include an aperture; drug release is only by diffusion through the second wall structure. As used herein, the terms "impermeable to the drug" and "impermeable to water" refer to the wall structure being substantially impermeable to the drug or to water, such that essentially no drug or water is released via the wall structure over the therapeutic release period. For use in the bladder, it is desirable that the device be compliant (i.e., easily flexed, soft feeling) during detrusor muscle contraction in order to avoid or mitigate discomfort and irritation to the patient. Thus, the durometer of the first and second materials of construction are a design consideration, and the proportion of a high durometer material may be limited in constructing a device housing of a given size while keeping it suitably compliant in the bladder. For example, Tecophilic™ thermoplastic polyurethane (Lubrizol Corp.) may have a Shore hardness greater than 70 A, such as from 80 A to 65 D, while silicone tubing which may have a Shore hardness of from 50 A to 70 A. Accordingly, it can be advantageous to utilize the combination of these two different polymeric materials, rather than making the device entirely of the water-swelling hydrophilic, drug-permeable second material.

The arrangement of the first and second wall structures can take a variety of forms. In certain embodiments, the first wall structure is a cylindrical tube and the second wall structure is an end wall disposed at least one end of the cylindrical tube, or the first wall structure and the second wall structure are adjacent one another and together form a cylindrical tube. That is, drug release is controlled by drug diffusion through a drug-permeable component defining a portion of the closed device housing. The drug-permeable wall structure may be located, dimensioned, and have material properties to provide the desired rate of controlled drug diffusion from the device. In some embodiments, the drug permeable wall may include a disk stabilized in the lumen of a tube at or near an end of the tube, optionally sandwiched between an inner washer and an outer washer. In some embodiments, the drug permeable wall is part of a sidewall of a tubular housing, or part of an end plug located at the end of a tubular housing.

The length and width of the wall portion formed of the water permeable material may be selected to provide a desired rate of water flux into the reservoir defined by device housing. In one embodiment, the width of the water permeable wall portion may be quantified by the arc angle defining the wall when viewed in cross-section normal to the luminal axis. The water permeable region(s) of the device housing can be controlled to give a selected area of, and thus rate for, osmotic water imbibition, and yet advantageously maintain suitable overall dimensions and elasticity of the device, formed of suitable biocompatible elastomers. Advantageously by forming the device housing by a co-extrusion process, the structural variations of the water permeable region(s) can be created with conventional co-extrusion equipment by selection of the processing parameters, thereby beneficially providing the ability to cost-effectively manufacture multiple structural device configurations. In some embodiments, the length of the water permeable regions(s) runs along only a portion of the overall length of the device. In such an embodiment, larger arc angles of the water permeable region(s) can therefore be employed while keeping the rate of drug release at a desirable level over an extend period of time. Such intravesical device housings are described, for example, in US 2016/0310715.

In some embodiments, the wall may have a varied thickness over the circumference of the wall, for example the drug permeable portion may have a thickness that is less than the thickness of the drug impermeable portion. Moreover, the thinner drug permeable wall structure may be disposed at various positions relative the adjacent, thicker drug impermeable wall structure. In some embodiments, drug release is controlled by drug diffusion through a drug-permeable component defining a portion of the closed device housing. The drug-permeable wall structure may be located, dimensioned, and have material properties to provide the desired rate of controlled drug diffusion from the device.

In some embodiments, the drug delivery device comprises a housing comprising a first wall structure and a second wall structure that are adjacent one another and together form a tube defining a drug reservoir lumen; and a drug contained in the drug reservoir lumen, wherein: (i) the second wall structure, or both the first wall structure and the second wall structure, are permeable to water, (ii) the first wall structure is impermeable to the drug and the second wall structure is permeable to the drug, such that the drug is releasable in vivo by diffusion through the second wall structure, (iii) the second wall structure comprises less than 90 percent of a cross sectional area of the tube, in a cross section normal to the longitudinal axis of the tube, (iv) and the first wall structure comprises a first polyurethane composition.

In some embodiments, the device comprises an elongated, elastic housing having a drug reservoir lumen extending between a first closed end and a second closed end; and a drug contained in the drug reservoir lumen, wherein (i) the housing comprises a tubular wall structure which comprises: a first annular segment formed entirely of a first material which is impermeable to the drug, and a second annular segment formed at least partially of a second material which is permeable to the drug and configured to release the drug in vivo by diffusion through the second material in the second annular segment, and (ii) the first annular segment has a first end which is integrally formed and connected with a first end of the second annular segment.

In some embodiments, the walls that define the drug reservoir lumens may have varying thickness. Housings with walls of different thicknesses may improve the housing's flexibility, compressibility, or both. Different wall thicknesses also may aid in securing a solid drug unit in the drug reservoir lumens.

In some embodiments, the intravesical device body, or housing, may include openings (e.g., at the opposed ends of an annular tube) in need of sealing following loading of the drug reservoir with the drug payload, during the assembly process. Any of these defined openings or ends of the housings, including the monolithic housing and modular housing units, may be sealed, if desired to close off an opening. This sealing may be accomplished with a sealing substance or structure. The sealing structure may be formed of biocompatible material, including a metal such as stainless steel, a polymer such as silicone, a ceramic, or sapphire, or adhesive, among others or combinations thereof. The sealing substance or structure may be biodegradable or bioerodible. In one embodiment, a medical grade silicone adhesive or other adhesive is loaded into the opening in a fluid or workable form and then cure within the housing opening to seal it. In some embodiments, the housing includes one or more predefined apertures for release of the drug from the device. These drug-release apertures are not the defined openings which are sealed. In other embodiments, the housing does not include a predefined drug-release aperture.

In some embodiments the device releases drug without a predefined drug release aperture (i.e., orifice). Release of drug from a device without a predefined drug-release aperture may be driven by diffusion or osmotic pressure. Examples of such suitable "no-orifice" release systems are described in PCT Patent Application Publication No. WO 2014/144066 (TB 130) and U.S. Patent Application Publication No. 2014/0276636 (TB 134), which are incorporated herein by reference.

In some embodiments, the drug delivery device includes an osmotic system as described in U.S. Publication 2016/0199544, U.S. Pat. No. 8,679,094, and U.S. Publication 2016/0008271, which are herein incorporated by reference.

In some embodiments, the drug delivery device includes an osmotic system as described in U.S. Publication 2016/0279399 (TB 137), which is herein incorporated by reference. In some embodiments using such systems, trospium may be loaded into the device housing in a liquid form prior to insertion of the device into the bladder of the individual.

In some embodiments, the device comprises a housing defining a reservoir; a first unit contained within the reservoir, the first unit comprising a drug; and a second unit contained within the reservoir in a position distinct from the first unit, wherein the second unit comprises a functional agent that facilitates in vivo release of trospium from housing. In some embodiments, the device comprises a housing defining a reservoir; a first unit contained within the reservoir, the first unit comprising a drug; and a second unit contained within the reservoir in a position distinct from the first unit, wherein the second unit comprises a functional agent that facilitates stabilization of trospium in urine in the bladder (i.e., anti-protease agent). In some embodiments, the first unit comprises one or more solid tablets or powders which comprise at least one drug (e.g., trospium, such as gemcitabine), and the second unit comprises one or more solid tablets or powders (e.g., which comprise an osmotic agent, such as urea). In some embodiments, the housing is in the form of an elongated elastomeric tube having a lumen (i.e., the reservoir) in which all of the solid tablets of the first and second units are aligned and contained. The diameter of the solid tablets may be substantially the same as the diameter of the lumen.

When osmotic release is the desired drug release mode, the functional agent in the second units may include an osmotic agent that facilitates osmotic release of the drug. For example, the osmotic agent may have a higher solubility than the drug, such that the osmotic agent expedites solubilization and/or subsequent release of the drug. This beneficially allows for the delivery of low solubility or other drugs typically only delivered via diffusion, from osmotic delivery-based devices. The device may exhibit an induction period while a sufficient volume of functional agent and/or drug are solubilized to achieve the osmotic pressure gradient.

Subsequently, the device may exhibit a zero-order release rate for an extended period, followed by a reduced, non-zero-order release rate over a decay period. A desired delivery rate can be achieved by controlling/selecting various parameters of the device, including but not limited to the surface area and thickness of the water permeable wall; the permeability to water of the material used to form the wall; the shape, size, number and placement of the apertures; and the dissolution profiles of the drug and functional agent.

The devices described herein may also be configured to release drug via diffusion, alone or in combination with osmotic release. The device may be configured to allow the solubilized drug to pass through a portion of the housing or one or more apertures therein.

Alternatively, or in combination with a water permeable wall portion, the housing may include at least one aperture configured to permit a fluid to enter the reservoir in vivo. The housing may also include one or more apertures or passing pores configured to permit solubilized drug to pass there through.

In some embodiments of the osmotic system, the device housing includes a first elastomeric material that is water permeable and a second elastomeric material that is water impermeable, wherein both materials are selected to be impermeable to the drug contained in the housing.

Figure 7C:
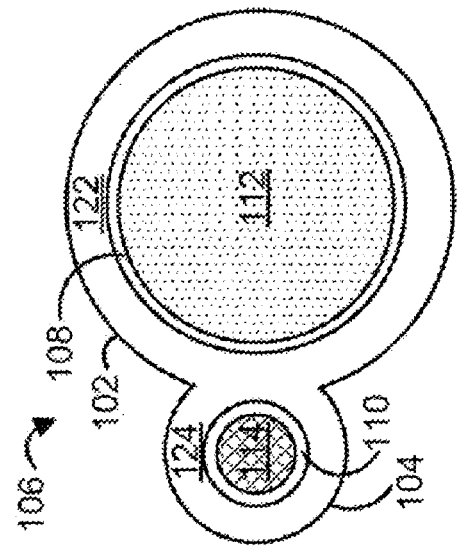
FIGS. 7A-7C show an intravesical device that can be used to provide local and continuous delivery of trospium or another therapeutic agent.
Figure 7A:
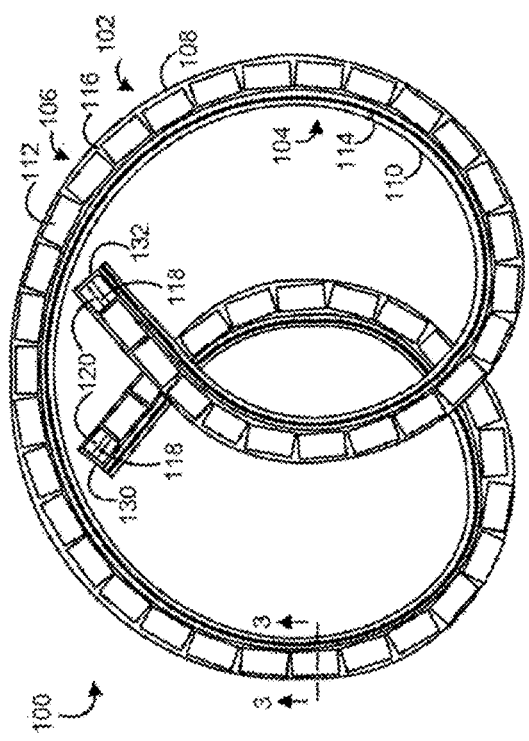
Figure 7B:
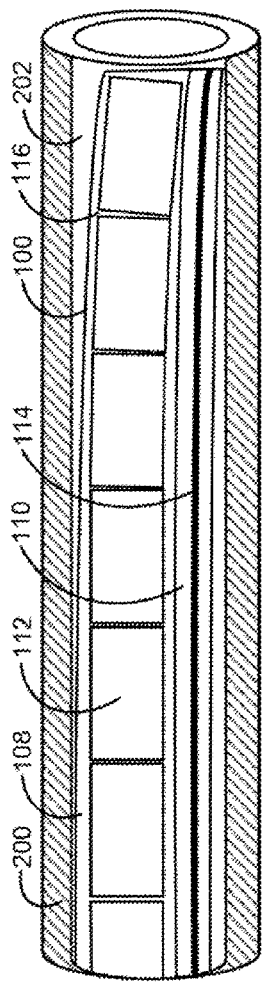

FIGS. 7A-7C illustrate one embodiment of an intravesical device useful in the methods described herein. The device 100 includes a drug reservoir portion 102 and a retention frame portion 104. In FIG. 7A, the device 100 is shown in a relatively expanded shape suited for retention within the urinary bladder of an individual. In FIG. 7C, the device 100 is shown in a relatively lower-profile shape for deployment through the working channel 202 of a deployment instrument 200, such as a cystoscope or other catheter, e.g., for insertion into and through the urethra and into the bladder of the patient. Following deployment (release of the device) into the bladder, the device 100 may assume the relatively expanded shape to retain the drug delivery device in the bladder. In the illustrated embodiment, the drug reservoir and retention frame portions 102, 104 of the drug delivery device 100 are longitudinally aligned and are integrally formed or otherwise coupled to each other along their length.

The drug delivery device 100 includes an elastic or flexible device body 106 that defines a drug reservoir lumen 108 and a retention frame lumen 110. The drug reservoir lumen 108 is configured to house a drug (e.g., trospium) which is in the form of a plurality of solid drug units 112, to form the drug reservoir portion 102. Interstices 116 or breaks formed between adjacent drug units 112 permit the drug units 112 to move with reference to each other so that the device 100 is flexible despite being loaded with drug in solid form. The retention frame lumen 110 is configured to house a retention frame 114 to form the retention frame portion 104.

As shown in the cross-sectional view of FIG. 7B, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed.

As shown in FIG. 7A, the drug reservoir lumen 108 is loaded with a number of drug units 112 in a serial arrangement. For example, between about 10 and about 100 drug units 112 may be loaded, such as between about 20 and about 80 drug units 112. The drug units may, for example, be tablets, beads, or capsules. Essentially any number of drug units may be used, depending upon the sizes of the reservoir and the drug units. The drug reservoir lumen 108 includes open ends 130 and 132, which are shown as relatively circular openings at opposite ends of the drug reservoir lumen 108. At least one of the openings provides ingress for the drug units 112 to be placed into the drug reservoir lumen 108 during device loading and assembly.

End plugs 120 block openings 130 and 132 following loading of the drug units 112. The end plugs 120 may be cylindrical and may be secured in the drug reservoir lumen 108 by frictional engagement and/or an adhesive or other fastening means. Each end plug 120 includes an aperture 118, as illustrated, to provide a passageway for releasing drug from the drug reservoir lumen 108. In some alternative embodiments, only one of the end plugs includes an aperture. In some other alternative embodiments, neither of the end plugs includes an aperture, and in some of those embodiments, the tube wall 122 includes a defined aperture for release of drug therethrough.

The retention frame lumen 110 is loaded with the retention frame 114, which may be an elastic wire, such as a nitinol wire, (thermally) shape-set into the overlapping coiled shape shown in FIG. 7A. The retention frame 114 may have an elastic limit and modulus that allows the device 100 to be introduced into the body in a relatively lower-profile shape, permits the device 100 to return the relatively expanded shape once inside the body, and impedes the device from assuming the relatively lower-profile shape within the body in response to expected forces, such as the hydrodynamic forces associated with contraction of the detrusor muscle and urination.

e. Erosion-Based Systems

In some embodiments, which may be used with tablets comprising low-solubility drugs, the drug is provided in tablet form secured in the device with exposed tablet faces, such that release of drug from the device occurs by controlled erosion/dissolution, as described in U.S. Pat. No. 9,107,816. In some embodiments, the device may comprise modular housings. The modular housings are typically formed from at least two separate housing units, each unit housing at least one solid drug unit. The material from which each housing unit is formed defines at least one drug reservoir lumen capable of housing a solid drug unit. The drug reservoir lumens may have one or more defined openings. For example, the drug reservoir lumen may have two opposed openings which expose correspondingly opposed end surfaces of the at least one solid drug unit housed therein. In certain embodiments, the at least two separate housing units in the modular housings are connected, directly or indirectly, by a retention frame. In some embodiments, the modular housing units may be placed on the retention frame to form a "bracelet" design. The devices may have one housing unit or a plurality of housing units. The number of housing units may be limited only by the size of the retention frame by which they are connected.

In some embodiments, one or more of the separate housing units includes a retention frame lumen through which a shared retention frame is extended. In certain embodiments, the retention frame lumen and the drug reservoir lumen of each housing unit are arranged parallel to each other. In particular embodiments, the retention frame lumen and the drug reservoir lumen of each housing unit are arranged perpendicular to each other. In further embodiments, the retention frame lumen and the drug reservoir lumen of each housing unit are arranged at an angle other than 0° (parallel) and 90° (perpendicular), such as 5, 10, 30, 45, 60, or 85°. In further embodiments, the devices described herein include two or more housing units with at least two of the following configurations: (1) the retention frame lumen and drug reservoir lumen are arranged substantially parallel to each other, (2) the retention frame lumen and drug reservoir lumen are arranged substantially perpendicular to each other, and (3) the retention frame lumen and drug reservoir lumen are arranged at an angle other than 0° (parallel) and 90° (perpendicular).

f. Integrated Silicone-Drug Delivery Systems

In some embodiments, the device may comprise an elastic polymer-drug matrix as described in WO2015/200752, which is herein incorporated by reference in its entirety.

g. Devices with Multiple Release Portions

In some embodiments, the device includes at least two drug release portions, at least one release portion releasing drug at a different rate than another release portion as described in WO2011/031855 which is herein incorporated by reference in its entirety. The release portions may achieve different release rates by having different configurations, by housing different drug formulations, or by employing different release mechanisms, among others or combinations thereof. The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

In some embodiments, the devices are loaded with drugs in the form of a number of solid drug tablets, which may be smaller in size than conventional drug tablets. Because the devices control release of the drug into the body, the drug itself may include little or no excipients that control drug release. Instead, the excipients present in the drug tablets may be present primarily or completely to facilitate the tableting process or solubilization in vivo. Thus, the devices may provide a high drug payload on a volume or weight basis, yet the devices may be small enough for in vivo deployment in a minimally invasive manner.

The drug housing also permits the egress of drug, in either liquid or semi-solid form as implanted or following in vivo solubilization. The wall may be formed from a drug-permeable material that permits drug efflux through the drug housing along its entire length. The wall also may be formed from a material that is semi-permeable to the drug depending at least in part on the drug form. For example, the wall may be permeable to the drug in one form, such as a charged form, but not another form, such as uncharged form (e.g., base form versus salt form). The wall also may include one or more openings or passageways formed completely through it that permit drug to exit the drug housing.

The drug portion can have any combination of the characteristics or configurations described herein, meaning the aperture may be provided, omitted, substituted with a passing pore, or augmented with additional apertures or passing pores; the housing may have a porous wall with an open-cell structure or a closed-cell structure; one or more degradable timing structures or release modulating structures may be associated with the housing, or any combination thereof.

The drug tablets may be aligned in any arrangement other than a serial arrangement, depending on the configuration of the drug housing. The drug tablets may fill any portion of the drug housing other than the entire drug housing as illustrated. A filling material such as silicone adhesive can be used to fill any portion of the drug housing that is not loaded with drug tablets, or air may be used, increasing the buoyancy of the device. The composition of the drug tablets may be the same or may vary along the device. The drug also may be in forms other than a drug tablet, such as other liquid, semi-solid, or solid forms (e.g., granules).

In some embodiments, the drug delivery device includes at least two discrete or segregated drug portions associated with a single retention portion. The drug portions may be separate drug housings each associated with the retention portion, or the drug portions may be separate areas within a single drug housing that is associated with the retention portion.

Each drug portion may be defined by a portion of the wall of the drug housing and at least one partition structure, which separates the drug portion from a second drug portion. The partition structure may be a plug inserted into the housing, such as a cylinder, sphere, or disk, among others, which is secured in place due to its size or with an adhesive. The partition structure also may be a portion of the housing formed directly therein, such as by molding.

A device with at least two discrete portions may be suited for controlled release of at least two drug payloads from a corresponding number of drug reservoirs. The two discrete portions may have the same configurations or different configurations as described herein. The two drug payloads may be the same as each other or may differ from each other with reference to content, such as active ingredient content or excipient content; form, such as salt form or base form; state, such as liquid, semi-solid, or solid state; among others or combinations thereof. Thus, the two discrete portions may release the two drug payloads at the same time or at different times, at the same rate or at different rates, via the same release mechanisms or different release mechanisms, or any combination thereof.

For example, one drug portion may be configured to release its drug payload relatively quickly after implantation and another drug portion may be configured to experience an induction time before beginning release, or a combination thereof. The onset of release of two payloads in different drug portions can be staged. Examples of quick release drug portions include a drug portion that operates as a relatively fast-acting osmotic pump, such as a silicone tube having a relatively thinner wall, a drug portion that is loaded with drug in a quick release form, such as liquid form or a specially formulated solid form, a drug portion associated with a relatively fast-acting degradable timing structure, or combinations thereof. Thus, the device may release drug during an initial, acute phase and during a maintenance phase.

As another example, one drug portion may be configured to release its drug payload at a relatively faster rate than the other drug payload. For example, one drug portion may house a drug payload with low water solubility for diffusive release that is initiated relatively soon after implantation, and another drug portion may house a drug payload that is highly water soluble for osmotic release after an induction period. As another example, one drug portion may house a drug payload in a liquid state for quick release through an aperture having a fast-acting degradable timing membrane, and another drug portion may house another drug payload of solid tablets for slow release following solubilization in vivo. As still another example, one drug portion may have a relatively solid wall while another drug portion may have a number of apertures or pores formed through its wall, which may increase the release rate due to diffusion, or a closed-cell porous wall, which may increase the release rate due to increased permeation of water or drug through the wall.

The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

By combining multiple distinct drug portions in a single device, the device may exhibit a desired release profile of trospium. The release profile from the device as a whole may be the sum of the release profiles of the discrete portions, for example, with the first portion exhibiting minimal lag time before the onset of release, the second portion exhibiting a short induction period as the osmotic pressure gradient develops, and the third portion exhibiting a longer delay before onset as the degradable structure dissolves or degrades. Once release begins from any one portion, the release rate may be relatively zero-order for an extended period, followed by a period of decay. It should be noted that the three discrete portions are examples, and that any number or combination of discrete portions may be used to achieve the desired release profile.

Because the different drug portions may be merely segregated areas within in a single tubular housing, the device advantageously may be relatively simple to construct and deploy, and yet the different drug portions exhibit different release profiles due to the different drug payloads, aperture placement, and degradable timing structures. In other embodiments in which the drug portions use, for example, walls of different materials, thicknesses, or porous cell structures, the housing may vary along its length or separate drug housings may be used. Thus, controlled release may be achieved in a range of manners.

II. Gels

In another embodiment, a coating substance may be intravesically applied to the bladder wall (e.g., to an area of the urothelium inside the urinary bladder), wherein the coating substance includes trospium and one or more excipient materials that promote adherence of the coating substance to the bladder wall and provides continuous controlled release of trospium over the treatment period. The coating substance may be a mucoadhesive formulation, such as gels, ointments, creams, pastes, films, emulsion gels, tablets, polymers, or a combination thereof. Mucoadhesive formulation polymers may include hydrogels or hydrophilic polymers, polycarbophil (e.g., Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof. A coating substance may be deployed in the bladder so that the coating substance engages the bladder wall.

The coating substance may be deployed in the bladder using a deployment instrument. The deployment instrument may be any device designed to navigate natural lumens of the body to reach the intended implantation site. For deployment in the bladder, the deployment instrument may be sized and shaped for passing through the individual's urethra or suprapubic cystostomy or suprapubic catheter to the individual's bladder. The deployment instrument may be a known device, such as a catheter or cystoscope, or a specially designed device. The deployment instrument is used to deploy the coating substance into the body and is subsequently removed from the body, leaving the coating substance wholly implanted in the body. Once so implanted, the coating substance may release drug into the body for an extended period. A comparable procedure can be used to deploy any of the devices or drugs described herein into other parts of the body through other natural lumens. For example, a deployment instrument can be used to deploy a liquid drug or drug formulation into the bladder by passing the deployment instrument through a urethra or suprapubic cystostomy.

EXAMPLES

Example 1: Intravesical Delivery of Trospium for Treatment of Overactive Bladder The purpose of this study was to confirm a sustained local delivery of trospium with Trospium-Releasing Intravesical System (TAR-302). TAR-302 is a passive, nonresorbable trospium-releasing intravesical system whose primary mode of action is the controlled release of trospium into the bladder over a period of time, for example, a 42-day period.

I. Part A.

Ten subjects were included in this study. These subjects were idiopathic overactive bladder patients who have failed oral medications. TAR-302 was placed into the bladder through an inserter on Study Day 0 and was removed on Study Day 42. TAR-302 releases trospium gradually during the 42 day indwelling time in a dose of about 4 to 8 mg per day in the bladder. See FIG. 3A.

Figure 8:
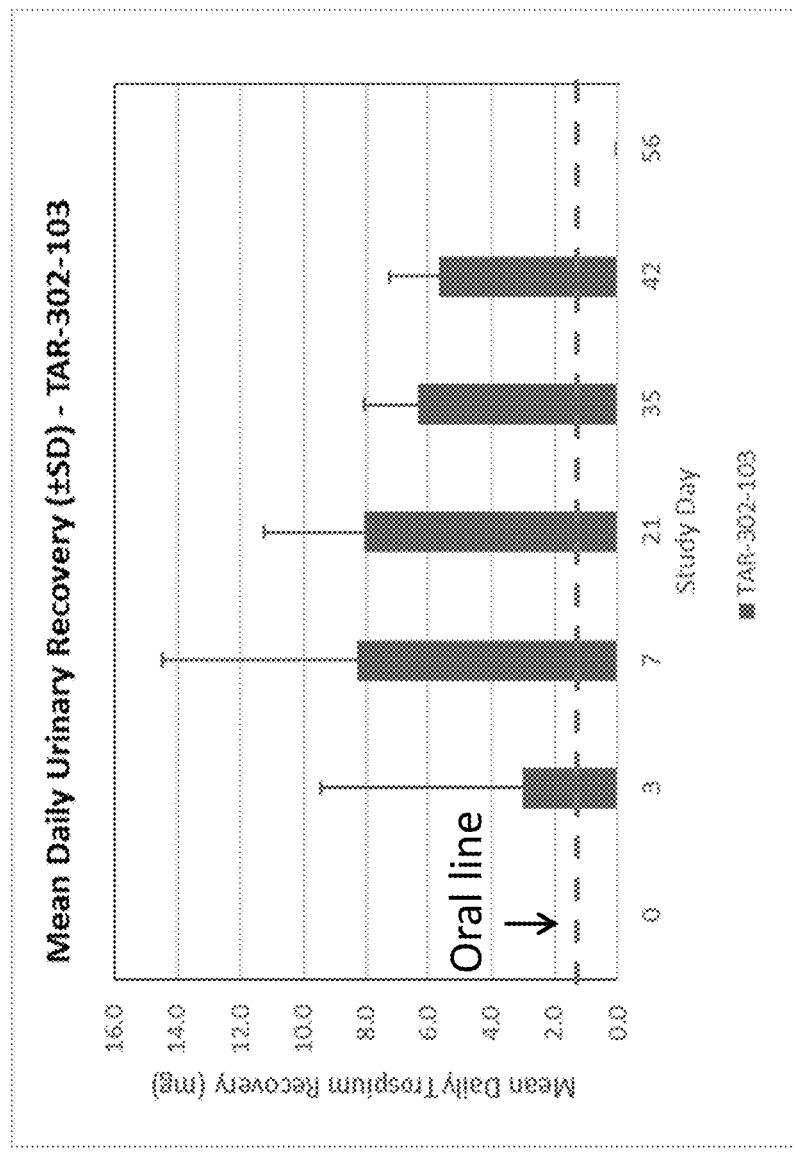
FIG. 8 shows daily urinary recovery of trospium assessed on Day 3, 7, 21, 35, 42 and 56 after the insertion of TAR-302.

Daily urinary recovery of trospium was assessed on Day 3, 7, 21, 35, 42 and 56. Average total daily recovery of trospium on PK sampling days is about 6.28 mg/day, ranging from 3.03 to 8.31 mg/day. The gray dash line represents the estimated daily recovery of trospium with an oral trospium administration at a dose of about 20 mg BID or 60 mg QD1. See FIG. 8.

The TAR-302 therapy resulted in a benign adverse event profile. No evidence of classical antimuscarinic systemic side effects, retention, or encrustation was observed. At the end of dosing (i.e., Day 42), average daily incontinence episodes reduced from the baseline of 5.42 to 1.28. See FIG. 9B. The efficacy of TAR-302 in oral refractory patients is superior to Botox®, which resulted in a reduction of 2.7 in average daily incontinence episodes from baseline. See FIG. 10A. The efficacy of TAR-302 is also superior to oral treatments of VESIcare® (solifenacin succinate) and Detrol® LA (tolterodine tartrate), which respectively resulted in a reduction of 1.4 and 0.8 in average daily incontinence episodes from baseline. See FIG. 10B. More strikingly, a durable response was observed after the removal of TAR-302. At Day 84, six weeks after the removal of TAR-302, subjects averagely had 2.44 daily incontinence episodes, which is 55% less than the baseline of 5.42 episodes. See FIG. 9B.

Figure 11:
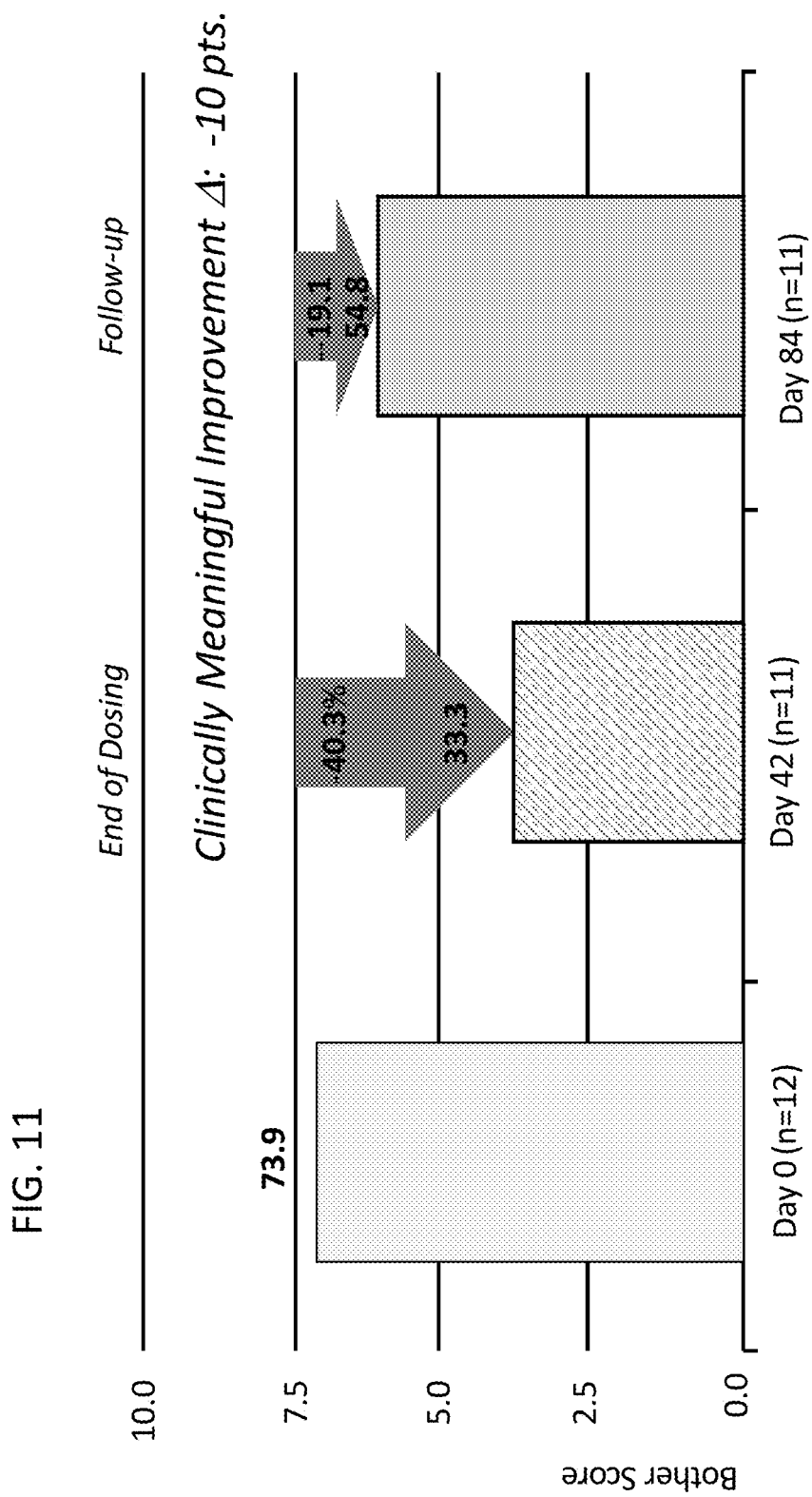
FIG. 11 shows the urinary bother score of individuals treated with TAR-302 calculated prior to treatment with TAR-302, at the end of dosing with TAR-302 at day 42, and 42 days after TAR-302 was removed at day 84.
Figure 12:
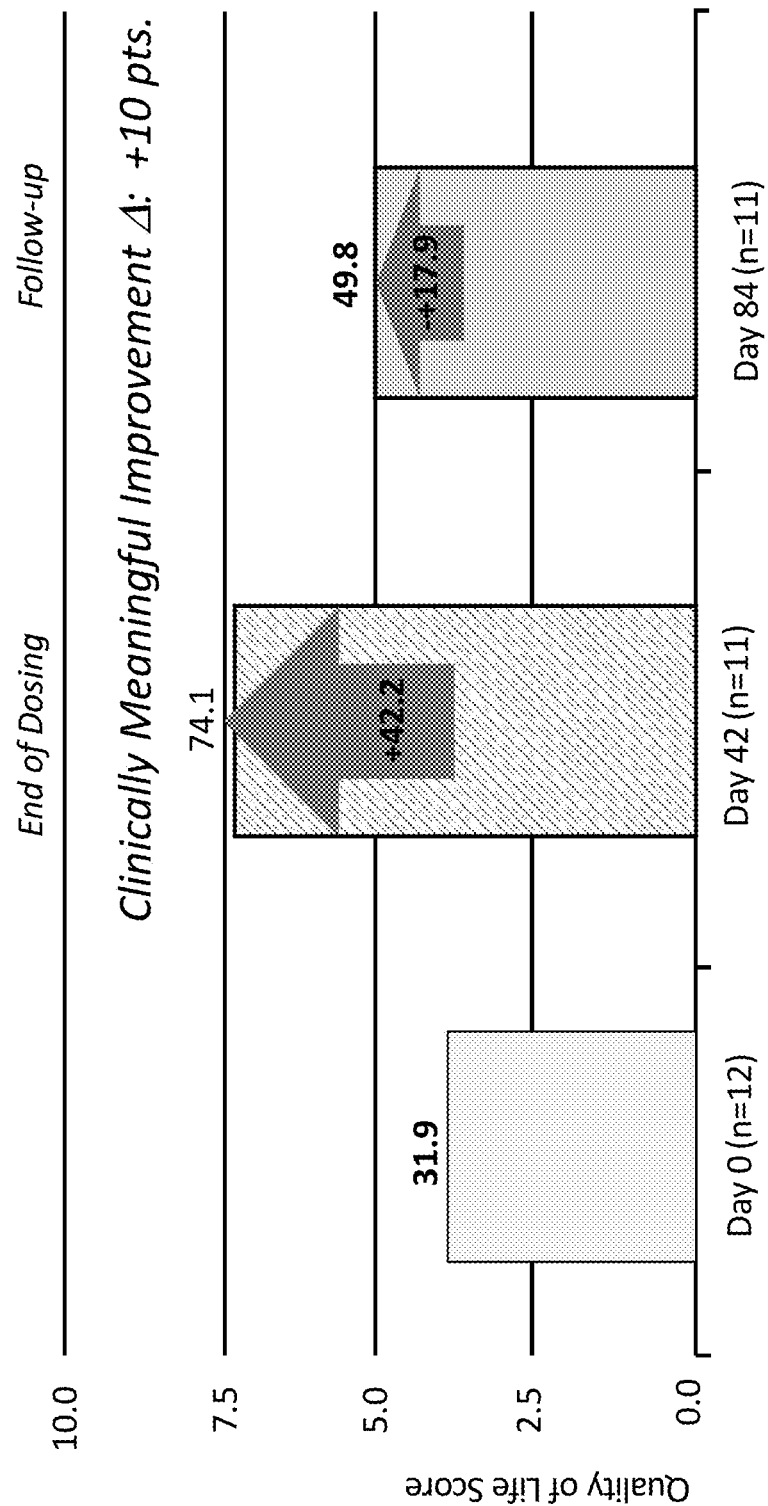
FIG. 12 shows the quality of life score of individuals treated with TAR-302 calculated prior to treatment with TAR-302, at the end of dosing with TAR-302 at day 42, and 42 days after TAR-302 was removed at day 84.

Urinary bother scores and quality of life scores were also significantly improved by TAR-302 as shown in FIGS. 11-12. After 42 days of treatment with TAR-302, a 40.3% decrease in bother score was observed. Six weeks after removal of TAR-302, the bother score was reduced by 19.1 points, a clinically meaningful improvement. FIG. 12. Similarly, at the end of the 42 day treatment period with TAR-302 a significant 42.2 point increase in quality of life score was observed. Even six weeks after removal of TAR-302, at day 84, a significant 17.9 point improvement of quality of life score was observed.

[1] According to Sanctura FDA label.

a. Outcome Measures

Primary Outcome Measures include safety of TAR-302 was assessed throughout the study based on reported adverse event (AE), investigational product events (IPEs), physical examinations (PEs), vital signs, clinical laboratory tests, scheduled cystoscopic examinations, bladder ultrasounds, bladder post-void residual volume (PVR), and the use of concomitant medications.

Secondary outcome measures include the following.
1. Tolerability of TAR-302 was assessed throughout the study based upon, for example, percent of subjects who were tolerant of TAR-302 indwelling for the designated period of time and did not require TAR-302 removal prior to the scheduled date of removal due to meeting any of the Subject Stopping Criteria or other drug or device constituent related adverse event.
2. Pharmacokinetic Analysis of Plasma and Urine was assessed from Day 0 to Day 56. For example, plasma trospium exposure and urinary trospium exposure were tested and analyzed.
3. Reduction in incontinence over baseline was assessed from Day 0 to Day 84. For example, a negative change from baseline in number of daily episodes of urinary incontinence, where incontinence is defined as an incident of involuntary loss of urine, was assessed and analyzed.
4. Reduction in daily micturition episodes was assessed from Day 0 to Day 56. For example, a negative change from baseline in the number of times a subject urinates into the toilet was assessed and analyzed.
5. Increase in voided volume per micturition was assessed from Day 0 to Day 56. For example, an increase over baseline as measured over separate 24-hour periods was assessed and analyzed.

Other Outcome Measures include Quality of Life (QoL) which was assessed from Day 0 to Day 84. For example, evidence of improvement in QoL were assessed by having the subject answering any or a combination of the following questions that during the past four weeks: a. the extent to which the subject was bothered by an uncomfortable urge to urinate; b. the extent to which the subject was bothered by a sudden urge to urinate with little or no warning; c. the extent to which the subject was bothered by accidental loss of small amounts of urine; e. the extent to which the subject was bothered by nighttime urination; f. the extent to which the subject was bothered by waking up at night because he/she had to urinate; g. the extent to which the subject was bothered by urine loss associated with a strong desire to urinate; h. how often have the subject's bladder symptoms caused the subject to plan "escape routes" to restrooms in public places; i. how often have the subject's bladder symptoms made the subject feel like there is something wrong with him/her; j. how often have the subject's bladder symptoms interfered with his/her ability to get a good night's rest; k. how often have the subject's bladder symptoms made him/her frustrated or annoyed about the amount of time he/she spent in the restroom; l. how often have the subject's bladder symptoms made him/her avoid activities away from restrooms (e.g., walking, running, hiking); m. how often have the subject's bladder symptoms awakened the subject during sleep; n. how often have the subject's bladder symptoms caused the subject to decrease his or her physical activities (exercising, sports, etc.); o. how often have the subject's bladder symptoms caused the subject to have problems with his/her partner or spouse; p. how often have the subject's bladder symptoms made the subject uncomfortable while traveling with others because of needing to stop for a restroom; q. how often have the subject's bladder symptoms affected his/her relationships with family and friends; r. how often have the subject's bladder symptoms caused him/her embarrassment; s. how often have the subject's bladder symptoms caused him/her to locate the closet restroom as soon as he/she arrive at a place he/she have never been.

b. Eligibility Criteria

Inclusion criteria include the following. 1. The subject has symptoms of overactive bladder (OAB) (frequency/urgency) with urge urinary incontinence or mixed urinary incontinence with a predominant urge component for at least 6 months. For example, the subject has eight or more voids per 24 hours as recorded in a diary, or at least 4 incontinence episodes associated with urgency recorded in a 3-day diary (the subject must have at least one episode that occurs each 24 hours or per day). 2. The subject has inadequate response or limiting side effects with anticholinergics for the treatment of OAB.

Exclusion criteria include the following. 1. Age of the subject is less than 18 years. 2. OAB is caused by a neurological condition. 3. There is significant renal dysfunction at screening (Glomerular Filtration Rate <30 mL/min). 4. There is significant polyuria of any cause at screening (urine output >4,000 mL/day). 5. There is a history of pelvic radiation. 6. There is a history of either bladder cancer or bladder pathology that the investigator deems unfit for study inclusion. 7. There is an active malignancy within 12 months with the exception of those with a negligible risk of metastasis or death treated with expected curative outcome. 8. The subject has any bladder or urethral anatomic feature that may prevent the safe placement, indwelling use, or removal of TAR-302. 9. In the opinion of the investigator, the subject has a history of significant stress urinary incontinence. 10. The subject has an active bladder stones or history of bladder stones <6 months prior to study entry. 11. The subject has a history of recurrent symptomatic urinary tract infections (UTIs) (>4 per 1 year). 12. The subject has either urinary retention or gastric retention or uncontrolled narrow-angle glaucoma. 13. The subject has a post-void residual volume (PVR) of 300 mL or greater. 14. The subject has a known hypersensitivity to trospium, chemically-related drugs, or component excipients. 15. The subject has a known hypersensitivity to the device materials, including silicone and nitinol. 16. The subject actively takes oral trospium. 17. The addition of a new or a change in dose to a current medication for the treatment of OAB (i.e. anticholinergics, beta-3 adrenergic agonists, antispasmodics, antidepressants, or hormones) within 30 days prior to signing the informed consent form (ICF). A stable dose must continue through the final study visit. If previously used and discontinued, these medications must have been stopped for >2 weeks prior to Day 0. 18. There is an intravesical onabotulinum toxin use within the last 9 months prior to the Screening Visit. 19. Intravesical anticholinergic medications were used within the last 30 days prior to the Screening Visit. 20. The subject has a history of non-medication based therapy (i.e. InterStim therapy) for the treatment of OAB. History of non-invasive neuromodulation (i.e. Percutaneous Tibial Nerve Stimulation (PTNS)) is allowed if discontinued at least 8 weeks prior to Study Day 0. 21. Female subject who is pregnant (as verified by urine test at time of screening) or lactating or of childbearing potential and not using acceptable methods of contraception. 22. The subject has a medical condition that may cause noncompliance with the study protocol. 23. The subject has participated in another drug, device, or behavioral study within 60 days prior to the Screening Visit. 24. The subject has a history or presence of any significant cardiovascular, pulmonary, hepatic, renal, gastrointestinal, gynecological, endocrine, immunological, dermatological, neurological or psychiatric disease or disorder that, in the opinion of the investigator, contraindicates participation. 25. History of any of the following within 3 months prior to Screening Visit. Major illness/major surgery (requiring hospitalization), including pelvic, lower back surgery or procedure unrelated to bladder cancer; most outpatient procedures are not exclusionary; renal or ureteral stone disease or instrumentation; Childbirth.

II. Part B.

This open label Phase 1 b study evaluated the safety, tolerability, and preliminary efficacy of TAR-302 in patients with idiopathic overactive bladder (iOAB) refractory or intolerant to oral therapy. Study subjects were required to have at least 4 incontinence episodes over 3 days at study entry. Subjects received a single administration of TAR-302 for 42 days of intravesical dwell time. TAR-302 was placed with an insertion catheter and removed via cystoscope. Pharmacokinetic (PK) analyses were conducted in blood and urine. Response to TAR-302 was assessed using 3-day voiding incontinence diaries and quality of life was assessed using the OAB-q Short Form (OAB-q SF).

Results

Eleven subjects successfully completed the study. Baseline characteristics are presented in Table 1. TAR-302 was well tolerated throughout the study: AEs potentially related to TAR-302 were all mild, and included hematuria (n=4), bladder discomfort (n=2), and bladder pain (n=2). There was only 1 AE observed typical of antimuscarinic exposure: a single report of transient dry mouth on day 36, which resolved spontaneously. 2 subjects experienced UTIs, which were considered potentially related to insertion procedures.

PK analyses demonstrated urine that trospium levels averaged 3.27 µg/mL across the study, well above predicted urine levels achieved with oral trospium (0.5-1 µg/mL) (See Sanctura FDA Package Insert, accessed March 2019). These intravesical concentrations produced negligible systemic exposure (average: 0.22 ng/ml).

TABLE 1

Demographics

| Demographic | Total |
|---|---|
| Age (median) | 60 (range: 54-66) |
| Female | 11 (100%) |
| Race | |
| Caucasian | 9 (81.8%) |
| Black/African American | 2 (18.2%) |
| BMI (median) | 29.3 (23.0-43.7) |

Subjects experienced a reduction in mean daily urge incontinence (UI) episodes of 75%, from 5.57 events per day at baseline to 1.4 events at Day 42 ($p<0.01$). 3 of the 11 subjects were fully continent at Day 42. Subjects also experienced clinically and statistically significant improvements in both symptom bother and health-related quality of life, as measured by the OAB-q SF: mean scores on the symptom bother subscale decreased by 41 points (74 at baseline, 33 at day 42, $p<0.01$), and mean scores on the HRQOL subscale increased by 45 points (32 at baseline, 77 at day 42, $p<0.001$).

Surprisingly, subjects appeared to experience durable symptom benefit well after removal of TAR-302 at Day 42, despite no further therapeutic intervention during this period. Mean UI episodes remained significantly lower than baseline at Day 84 2.67 UI episodes/day, −52%, $p<0.05$); additional measures of UI improvement are noted in Table 2. Further, clinical (though not statistical) improvements on both OABq-SF subscales were also observed at Day 84: symptom bother decreased by 19 points (74 at baseline vs. 55 at Day 84), and HRQOL increased by 18 points (32 at baseline vs. 50 at Day 84; minimum clinically meaningful change=10 points).

TABLE 2

UI Responder Analysis

| Assessment Day | Statistic | Total (N = 11) |
|---|---|---|
| Pre-TAR-302 Removal (Day 42) | | |
| >50% decrease from baseline | n (%) | 9/11 (81.8) |
| >70% decrease from baseline | n (%) | 7/11 (63.6) |
| 100% decrease from baseline | n (%) | 3/11 (27.3) |
| Final Study Day (Day 84 +/− 7 days) | | |
| >50% decrease from baseline | n (%) | 5 (45.5) |
| >70% decrease from baseline | n (%) | 2 (18.2) |
| 100% decrease from baseline | n (%) | 0 (0.0) |

TAR-302 has demonstrated encouraging safety, tolerability, and preliminary efficacy in the management of symptoms for patients with urge urinary incontinence insufficiently controlled with oral therapies.

Example 2

In this study, TAR-302 is placed into the bladder of subjects with overactive bladder through an inserter on Study Day 0 and is removed on Study Day 56 immediately followed by another inserter of TAR-302, which is removed on Day 112. The subjects are further treated with TAR-302 on a prn (as need) basis.

I. Outcome Measures

Primary Outcome Measures include safety of TAR-302 assessed throughout the study based on reported adverse event (AE), investigational product events (IPEs), physical examinations (PEs), vital signs, clinical laboratory tests, scheduled cystoscopic examinations, bladder ultrasounds, bladder post-void residual volume (PVR), and the use of concomitant medications.

Secondary outcome measures include the following.
1. Tolerability of TAR-302 was assessed throughout the study based upon, for example, percent of subjects who were tolerant of TAR-302 indwelling for the designated period of time and did not require TAR-302 removal prior to the scheduled date of removal due to meeting any of the Subject Stopping Criteria or other drug or device constituent related adverse event.
2. Pharmacokinetic Analysis of Plasma and Urine assessed from Day 0 to Day 112. For example, plasma trospium exposure and urinary trospium exposure are tested and analyzed.
3. Reduction in incontinence over baseline assessed for the duration of participation in the study. For example, a negative change from baseline in number of daily episodes of urinary incontinence, where incontinence is defined as an incident of involuntary loss of urine, are assessed and analyzed.
4. Reduction in daily micturition episodes is assessed from Day 0 to Day 112. For example, a negative change from baseline in the number of times a subject urinates into the toilet is assessed and analyzed.
5. Increase in voided volume per micturition was assessed from Day 0 to Day 112. For example, an increase over baseline as measured over separate 24-hour periods is assessed and analyzed.

Other Outcome Measures include Quality of Life (QoL) which is assessed from Day 0 to Day 112. For example, evidence of improvement in QoL is assessed by having the subject answering any or a combination of the following questions that during the past four weeks: a. the extent to which the subject was bothered by an uncomfortable urge to urinate; b. the extent to which the subject was bothered by a sudden urge to urinate with little or no warning; c. the extent to which the subject was bothered by accidental loss of small amounts of urine; e. the extent to which the subject was bothered by nighttime urination; f. the extent to which the subject was bothered by waking up at night because he/she had to urinate; g. the extent to which the subject was bothered by urine loss associated with a strong desire to urinate; h. how often have the subject's bladder symptoms caused the subject to plan "escape routes" to restrooms in public places; i. how often have the subject's bladder symptoms made the subject feel like there is something wrong with him/her; j. how often have the subject's bladder symptoms interfered with his/her ability to get a good night's rest; k. how often have the subject's bladder symptoms made him/her frustrated or annoyed about the amount of time he/she spent in the restroom; l. how often have the subject's bladder symptoms made him/her avoid activities away from restrooms (e.g., walking, running, hiking); m. how often have the subject's bladder symptoms awakened the subject during sleep; n. how often have the subject's bladder symptoms caused the subject to decrease his or her physical activities (exercising, sports, etc.); o. how often have the subject's bladder symptoms caused the subject to have problems with his/her partner or spouse; p. how often have the subject's bladder symptoms made the subject uncomfortable while traveling with others because of needing to stop for a restroom; q. how often have the subject's bladder symptoms affected his/her relationships with family and friends; r. how often have the subject's bladder symptoms caused him/her embarrassment; s. how often have the subject's bladder symptoms caused him/her to locate the closet restroom as soon as he/she arrive at a place he/she have never been.

Example 3: A Prospective, Multi-Center, Open-Label Study of Trospium Delivered Intravesically by TAR-302-5018 to Subjects with Idiopathic Overactive Bladder (iOAB) and Urinary Incontinence—Part 1

TAR-302-5018 contains 850 mg of trospium chloride and has been shown to release an average of 10 mg/day over a 42-day indwelling period in in vitro studies. This average daily release rate is estimated to produce a urine concentration of 7 µg/mL in humans, assuming a urine production rate of 1500 mL/day.

I. Objectives

Objectives of the study includes evaluating the safety and tolerability of one dosing cycle of TAR-302-5018 for up to 42 days, evaluating the pharmacokinetics (PK) of trospium exposure in urine and plasma during the 42-day indwelling period of TAR-302-5018, and determining the effects of the intravesical continuous release of trospium on urinary incontinence, urinary symptoms (frequency of micturition episodes and void volume), and quality of life (QoL) symptoms.

II. Methodology

Subjects with iOAB with urge urinary incontinence refractory to or intolerant to oral anticholinergic therapy were screened for inclusion into the study. On Day 0, eligible subjects received TAR-302-5018 transurethrally by way of the TARIS Inserter. On Day 42, TAR-302-5018 was removed by way of either flexible or rigid cystoscopy. Subjects were followed during treatment for approximately 42 days after the removal of TAR-302-5018 for safety and efficacy assessments which were completed on Day 84 (±7 days). In addition, PK assessments were performed on the Day 0, Day 3 (±1 day), Day 7 (±1 day), Day 21 (±1 day), Day 35 (±2 days), Day 42, and Day 56 (±2 days) visits. Subjects were contacted by phone in between visits on Day 13 (±1 day), Day 27 (±1 day), Day 38 (±1 day), and Day 49 (±1 day) for safety assessments and reminders of study procedures.

Approximately 10 subjects were planned for inclusion in this part of the study. Twelve subjects were enrolled and underwent insertion of TAR-302-5018; these 12 subjects were included in the Intent-to-Treat (ITT) Population and Safety Population. Eleven subjects completed the study and were included in the Per-Protocol (PP) Population.

III. Diagnosis and Main Criteria for Inclusion

To be eligible to participate in this study, the subject must have met all of the following inclusion criteria at the time of enrollment: 1. Symptoms of overactive bladder (OAB) (frequency/urgency) with urge urinary incontinence or mixed urinary incontinence with a predominant urge component for at least 6 months. This means that the subject has 8 or more voids per 24 hours as recorded in a diary and/or at least 4 incontinence episodes associated with urgency recorded in a 3-day diary (or at least 1 episode must have occurred per each 24-hour day). 2. Inadequate response or limiting side effects with anticholinergics for the treatment of OAB.

A subject was not eligible for inclusion in the study if any of the following exclusion criteria applied: 1. Age <18 years. 2. OAB caused by neurological condition. 3. Presence of significant renal dysfunction at screening (glomerular filtration rate <30 mL/min). 4. Presence of significant polyuria of any cause at screening (urine output >4,000 mL/day). 5. History of pelvic radiation. 6. History of either bladder cancer or bladder pathology that the investigator deemed unfit for study inclusion. 7. Active malignancies within 12 months with the exception of those with a negligible risk of metastasis or death treated with expected curative outcome. 8. Subjects with any bladder or urethral anatomic feature that may have prevented the safe placement, indwelling use, or removal of TAR-302-5018. 9. In the opinion of the investigator, the subject had a history of significant stress urinary incontinence. 10. Subjects with active bladder stones or history of bladder stones <6 months prior to study entry. 11. History of recurrent symptomatic urinary tract infections (UTIs) (>4 per 1 year). 12. Subjects with either urinary retention or gastric retention or uncontrolled narrow-angle glaucoma. 13. A post-void residual volume (PVR) of 300 mL or greater. 14. Subjects with known hypersensitivity to trospium, chemically-related drugs, or component excipients. 15. Subjects with known hypersensitivity to the device materials, including silicone and nitinol. 16. Subjects actively taking oral trospium. 17. The addition of a new or a change in dose to a current medication for the treatment of OAB (i.e. anticholinergics, beta-3 adrenergic agonists, antispasmodics, antidepressants or hormones) within 30 days prior to signing the Informed Consent Form (ICF). A stable dose must have been continued through the final study visit. If previously used and discontinued, these medications must have been stopped for >2 weeks prior to Day 0. 18. Intravesical onabotulinum toxin use within the last 9 months prior to the Screening Visit. 19. Intravesical anticholinergic medications within the last 30 days prior to the Screening Visit. 20. History of non-medication based therapy (i.e., Interstim therapy) for the treatment of OAB. Non-invasive neuromodulation such as Percutaneous Tibial Nerve Stimulation (PTNS) was allowed if discontinued at least 8 weeks prior to Day 0. 21. Female subject who was pregnant (as verified by urine test at time of screening) or lactating or of childbearing potential and not using acceptable methods of contraception. 22. Subject had a medical condition that may have caused noncompliance with the study protocol. 23. Subject refused to provide written informed consent. 24. Subject was unable or unwilling to complete the questionnaires and/or diaries and attend all protocol mandated study visits. 25. Participation in another drug, device, or behavioral study within 60 days prior to the Screening Visit. 26. History or presence of any significant cardiovascular, pulmonary, hepatic, renal, gastrointestinal, gynecological, endocrine, immunological, dermatological, neurological or psychiatric disease or disorder that, in the opinion of the investigator, contraindicated participation. 27. History of any of the following within 3 months prior to Screening Visit: major illness/major surgery (requiring hospitalization), including pelvic, lower back surgery or procedure unrelated to bladder cancer; most outpatient procedures were not exclusionary; renal or ureteral stone disease or instrumentation; childbirth. 28. Difficulty providing blood samples. 29. Other unspecified reasons that, in the opinion of the investigator or TARIS, made the subject unsuitable for enrollment.

IV. Endpoints a. Primary Safety Endpoint.

Safety of TAR-302-5018 upon insertion, 42-day continuous exposure, and removal. Safety was assessed via treatment-emergent adverse events (TEAEs), clinical laboratory tests, vital signs, physical examinations, bladder ultrasound, Investigational Product Event (IPEs), bladder PVR assessments, cystoscopic examination, and concomitant medications.

b. Secondary Safety Endpoints

Tolerability of TAR-302-5018 upon insertion, 42-day continuous exposure, and removal. Tolerability was defined as: not requiring removal prior to the scheduled date due to meeting any of the protocol-specific Subject Stopping Criteria or other drug or device constituent related adverse event (AE). PK analysis of plasma and urine (based on samples from Day 0, Day 3 (±1 day), Day 7 (±1 day), Day 21 (±1 day), Day 35 (±2 day), Day 42, and Day 56 (±2 days). Plasma and urine samples were used to determine the following: Maximum concentration across visits (Cmax); Study Day of maximum concentration (Tmax); Concentration at removal on Day 42 (Ctau); Average concentration from Day 0 to 42 (Cave42); Average concentration from Day 0 to Day 56 (Cave56).

c. Preliminary Efficacy Endpoints.

Reduction in incontinence defined as a negative change from baseline in number of daily episodes of urinary incontinence, where an event of incontinence was defined as an incident of involuntary loss of urine, as recorded in a subject bladder diary during the 3 days prior to the Day 0 (baseline), Day 42, and Day 84 (±7 days) visits. Reduction in daily micturition episodes defined as a negative change from baseline in the number of times a subject urinates into the toilet, as recorded in a subject diary during one 24-hour period prior to the Day 0 (baseline), Day 3 (±1 day), Day 7 (±1 day), Day 21 (±1 day), Day 35 (±2 days), Day 42, and Day 56 (±2 days) visits. Exploratory assessment: increase in voided volume per micturition over baseline, measured over one 24-hour period prior to the Day 0 (baseline), Day 3 (±1 day), Day 7 (±1 day), Day 21 (±1 day), Day 35 (±2 days), Day 42, and Day 56 (±2 days) visits and recorded by the subject in the diary.

d. Additional Efficacy Endpoint

Evidence of improvement in QoL as assessed by the OAB-q Short Form which was completed at the study site on Day 0, Day 42, and Day 84 (±7 days).

V. Statistical Methods a. Analysis Populations.

ITT Population: Included all subjects enrolled and for whom the TAR-302-5018 insertion procedure on Day 0 was attempted, whether successfully performed or not.

PP Population: Included all subjects in whom the TAR 302-5018 insertion procedure was successfully performed and who retained TAR-302-5018 for the complete 42-day treatment period without major protocol deviations. Major protocol deviations were defined prior to database lock.

Safety Population: Included all subjects enrolled and for whom the TAR-302-5018 insertion procedure was successfully performed. For this study, the ITT and Safety Population were identical and results are presented for the ITT Population.

b. Sample Size Determination.

The sample size was not based on statistical considerations.

c. Efficacy.

The number of incontinence episodes for 3 days prior to the specified visits, the number of micturitions for 3 days prior to the specified visits, and the total urine volume voided over each 24-hour collection period were summarized descriptively by time point along with changes from baseline. A summary of subject response (subjects with a >50% decrease in incontinence episodes from baseline, a >75% decrease in incontinence episodes from baseline, and a 100% decrease in incontinence episodes from baseline) was presented for Day 42 and Day 84. Scores of the OAB-q Short Form were transformed as defined in the clinical study report. The transformed symptom severity scores and transformed health-related QoL scores were summarized descriptively by time point.

d. Pharmacokinetic.

Plasma and urine trospium were summarized descriptively by time point. Cmax, Tmax, Ctau, Cave42, and Cave56 for plasma and urine were summarized descriptively.

e. Safety.

AEs were coded using the Medical Dictionary for Regulatory Activities (MedDRA) version 20.0. TEAEs were summarized by MedDRA system organ class and preferred term. TEAEs were also summarized by severity, relationship (to drug constituent, device constituent, or TARIS Inserter), and time period (Day 0 through 42, Day 42 through the Day 49 [±1 day], and Day 0 through Day 49 [±1 day]). Serious adverse events (SAEs) were also summarized descriptively. Vital signs and laboratory assessments along with the changes from baseline were summarized descriptively. Physical examination dates were listed. The number of subjects who were tolerant was presented for the TAR-302-5018 indwelling period. IPEs were summarized descriptively. Bladder PVR results were summarized descriptively. Bladder ultrasound encrustation results were listed by subject. Cystoscopic assessments of bladder urothelium were listed by subject. Prior and concomitant medications were coded using the World Health Organization Drug Dictionary Enhanced (B3 Dec. 2017 version) and were summarized descriptively.

VI. Summary and Conclusions a. Efficacy Results

The mean number of incontinence episodes decreased by approximately 75% in the 3-day period prior to Day 42 and approximately 52% in the 3-day period prior to Day 84 (±7 days) in the PP Population when compared to baseline.

On Day 42, approximately 82% of subjects had a >50% decrease in incontinence episodes from baseline, 64% of subjects had a >75% decrease from baseline, and 27% of subjects had a 100% decrease from baseline in the PP Population. On Day 84 (±7 days), approximately 46% of these subjects reported a >50% decrease from baseline and 18% reported a >75% decrease from baseline.

The mean number of micturition episodes in a 24-hour period decreased from baseline at all post-baseline time points, with decreases of approximately 8%, 12%, 12%, 14%, 8%, and 11% were observed at Day 3 (±1 day), Day 7 (±1 day), Day 21 (±1 day), Day 35 (±2 days), Day 42, and Day 56 (±2 days), respectively, in the PP Population.

Mean 24-hour urine volumes decreased from baseline at Day 3 (±1 day), Day 7 (±1 day), Day 21 (±1 day), Day 35 (±2 days), Day 42, and Day 56 (±2 days) in the PP Population. However, these findings were observed along with decreases in bladder PVR.

Mean transformed symptom severity scores were decreased by approximately 55% at Day 42 and approximately 26% at Day 84 (+7 days) in the PP Population, indicating decreased subject-reported symptom severity.

Mean transformed Health-Related Quality of Life (HRQL) scores increased by approximately 143% at Day 42 and approximately 58% at Day 84 (+7 days) in the PP Population, indicating greater subject-reported QoL.

b. Pharmacokinetic Results

Following insertion of the TAR-302-5018 system, trospium urine concentrations were quantifiable in 9 of 11 subjects on Day 3 and in all 11 subjects in the PP Population on Day 7 (±1 day) (with a mean Day 7 concentration of 5258 ng/ml).

The majority of urine concentrations fell within the forecasted range of 2000 to 6000 ng/mL, and target concentrations were maintained through Day 42. Mean urine trospium concentrations were greatest on Day 21 (±1 day) (mean of 5265 ng/ml), declined to 3822 ng/ml at Day 35 (±2 days) and 3565 ng/ml at Day 42.

Detectable plasma concentrations were infrequent. Samples with measurable trospium plasma concentrations did not exhibit a consistent time course nor did the observed concentrations correlate with measured urine concentration, urine volume or amounts recovered. Following confirmatory analyses using an independent bioanalytical method, external contamination of plasma samples is suspected to have affected the findings of 2 of the samples with detectable trospium concentrations. Excluding these 2 samples, trospium concentrations across the study were consistently low (<0.7 ng/mL).

Overall, the urine and plasma concentrations for this study were generally consistent with findings in previous nonclinical studies.

c. Safety Results

TAR-302-5018 was well tolerated. No subjects were considered to be intolerant to TAR-302-5018, based on the protocol-specified definition of tolerability.

No subjects withdrew from treatment early due to either a TEAE or an IPE. One subject withdrew consent and discontinued TAR-302-5018 on Day 21, and the remaining 11 subjects continued use of TAR-302-5018 as planned through the Day 42 visit and completed the study.

The most common TEAEs during the treatment period of 42 days were hematuria (4/12 subjects; 33.3%), UTI (2/12 subjects; 16.7%), bladder pain (2/12 subjects; 16.7%), bladder discomfort (2/12 subjects; 16.7%), and sinusitis (2/12 subjects; 16.7%). The majority of AEs were mild.

One drug-related TEAE was reported: dry mouth. The most frequent device-related TEAEs were hematuria (4/12 subjects; 33.3%), bladder discomfort (2/12 subjects; 16.7%), and bladder pain (2/12 subjects; 16.7%). Two subjects reported at least one TARIS Inserter-related TEAE. The events included: nausea, vomiting, chills, pyrexia, UTI, increased white blood cell count, lactic acidosis, dysuria, hematuria, and perinephric edema, all in one subject (8.3%), and 1 report of urethral pain in the other subject (8.3%).

Mean changes from baseline in laboratory parameters were generally small. Post-baseline findings of occult blood (at any level) were greatest at Day 21 (±1 day) (41.7%) and decreased to 27.3% at Day 42 and 9.1% at Day 84 (±7 days). Four subjects had hematuria findings that were reported as TEAEs; one of these reports was in the subject with the SAE of UTI.

Mean changes from baseline in blood pressure, heart rate, respiratory rate, and body temperature were small and not clinically meaningful. No subjects had a TEAE related to a vital sign abnormality.

Mean bladder PVR decreased from screening by approximately 21%, 42%, and 29% at Days 7 (±1 day), 21 (±1 day), and Day 35 (±2 days), respectively.

There were no observations of urothelial bleeding, no evidence of bladder stones, and no evidence of bladder diverticula were observed upon cystoscopy. No cases of encrustation were observed upon bladder ultrasound assessments on Day 21 (±1 day) or upon removal.

One IPE was reported, which included damage to the TAR-302-5018 which the investigator suspected occurred while grasping the system for removal. The subject did not report discomfort or any other TEAEs.

d. Conclusion.

Overall, TAR-302-5018 was found to have an acceptable safety profile, was well tolerated over the 42-day indwelling period, and consistently produced urine concentrations in the targeted and expected range, with limited systemic exposure. Notable decreases in the number of urge urinary incontinence episodes were observed in this patient population, along with decreases in the number of micturitions, decreases in subject-reported symptom severity scores, and improvements in QoL. The greatest effects were observed at Day 42, however, persistent and meaningful improvements from baseline were still evident at the final study assessment occurring 6 weeks after removal of TAR-302-5018.

Example 4: A Prospective, Multi-Center, Open-Label Study of Trospium Delivered Intravesically by TAR-302-5018 to Subjects with Idiopathic Overactive Bladder (iOAB) and Urinary Incontinence—Part 2

Trospium-Releasing Intravesical System (TAR-302-5018) is placed into the bladder through an inserter on Study Day 0 and is removed on Study Day 84. TAR-302-5018 releases trospium gradually during the 84 day indwelling time.

I. Outcome Measures

Safety of TAR-302-5018 was assessed on days 0, 14, 56, 84, and 112, as shown in FIG. 15A. Safety was assessed throughout the study based on reported AEs, investigational product events (IPEs), physical examinations (PEs), vital signs, clinical laboratory tests, scheduled cystoscopic examinations, bladder ultrasounds, bladder post-void residual volume (PVR), and the use of concomitant medications.

Tolerability of TAR-302-5018 was assessed. Percent of subjects who are tolerant of TAR-302-5018 indwelling for the designated period of time and do not require TAR-302-5018 removal prior to the scheduled date of removal due to meeting any of the Subject Stopping Criteria or other drug or device constituent related adverse event.

Pharmacokinetic Analysis of Plasma and Urine [Time Frame: From Day 0 to Day 112] was conducted. It includes analysis of plasma trospium exposure and urinary trospium exposure.

Reduction in incontinence over baseline [Time Frame: From Day 0 to Day 112] was assessed. A change from baseline in number of daily episodes of urinary incontinence was assessed, where incontinence is defined as an incident of involuntary loss of urine.

Reduction in daily micturition episodes [Time Frame: From Day 0 to Day 112] was assessed. A change from baseline in the number of times a subject urinates into the toilet was be assessed.

Increase in voided volume per micturition [Time Frame: From Day 0 to Day 112] was assessed. A change from baseline as measured over separate 24-hour periods was be assessed.

Other outcome measures include quality of life score and bother score as assessed by the OAB-q short form.

II. Inclusion Criteria

Patients with symptoms of idiopathic overactive bladder (iOAB) (frequency/urgency) with urge urinary incontinence or mixed urinary incontinence with a predominant urge component for at least 6 months were be included. These patients may have 8 or more voids per 24 hours as recorded in a diary or at least 4 incontinence episodes associated with urgency recorded in a 3-day diary (or at least 1 episode occurs per each 24 hour day).

Patients were also be included if, in the opinion of the investigator, the subject has experienced an inadequate response to or limiting side effects with prior oral medications for the treatment of OAB.

III. Exclusion Criteria

Patients that fulfill any of the conditions listed below were excluded. 1. Age <18 years. 2. Neurologic bladder condition. 3. Subjects with Diabetes Mellitus (both Type 1 & Type 2) must demonstrate optimal glycemic control with HbA1c levels <7.5% and an absence of significant glucosuria defined as 3+ glucose via dipstick at screening. 4. Presence of significant polyuria of any cause at screening (urine output >3,000 mL/day). 5. Presence of nocturnal polyuria at time of study screening defined as >30% of total 24-hour urine collected from time of evening (P.M.) sleep and inclusive of the first morning (A.M.) void. 6. History of pelvic irradiation. 7. History of either bladder cancer or bladder pathology that the investigator deems unfit for study inclusion. 8. Currently uses intermittent catheterization (IC) to empty the bladder within 30 days of Day 0. 9. Subjects with any bladder or urethral anatomic feature (e.g., urethral stricture) that in the opinion of the investigator may prevent the safe placement, indwelling use, or removal of IP. 10. Subjects with active bladder stones or history of bladder stones <6 months prior to study entry. 11. Gross hematuria within 30 days of Day 0. 12. History of uncontrolled bleeding, bleeding diathesis, or underlying coagulopathy within 30 days of Day 0. 13. In the opinion of the investigator, the subject has a history of predominance of significant stress urinary incontinence. 14. History of >2 symptomatic urinary tract infections in the 6-months prior to Day 0. 15. Subjects with either urinary retention or gastric retention or uncontrolled narrow-angle glaucoma within 90 days of Day 0. 16. A post-void residual volume (PVR) of 100-mL or greater. 17. Subjects with known hypersensitivity to trospium, chemically-related drugs, or component excipients. 18. Subjects with known hypersensitivity to the device materials, including silicone and nitinol. 19. Anticholinergic or beta-3 agonist use for the treatment of urge urinary incontinence <2 weeks prior to Day 0. 20. History of intravesical onabotulinum toxin use within the last 9 months prior to the Screening Visit. 21. Intravesical anticholinergic medications within the last 14 days prior to the Screening Visit. 22. History of procedural-based neuromodulation therapy (e.g. InterStim therapy, Percutaneous Tibial Nerve Stimulation [PTNS]) for the treatment of OAB. 23. Female subject who is pregnant (as verified by serum test at time of screening) or lactating. 24. Subject has, in the opinion of the investigator, a medical condition that may cause noncompliance with the study protocol. 25. Subject who is unable or unwilling to complete the questionnaires, diaries, or attend all protocol mandated study visits. 26. Participation in another drug, device, or behavioral study within 60 days prior to the Screening Visit. 27. History or presence of any significant cardiovascular, pulmonary, hepatic, renal, gastrointestinal, gynecological, endocrine, immunological, dermatological, neurological or psychiatric disease or disorder, or other unspecified reasons that, in the opinion of the investigator or TARIS, make the subject unsuitable for enrollment. 28. History of any of the following within 3 months prior to Screening Visit: i. Major illness/major surgery (requiring hospitalization), including pelvic, lower back surgery or procedure; most outpatient procedures are not exclusionary; ii. Childbirth. 29. History of prostatic biopsy or surgery (ablative or non-ablative) within 6 months prior to Day 0. 30. History of significant pelvic organ prolapse (Grade >/=3). 31. Difficulty providing blood samples. 32. Known history of drug or alcohol dependency within 12 months of screening. 33. Other unspecified reasons that, in the opinion of the investigator or TARIS, make the subject unsuitable for enrollment Daily incontinence events were assessed on days 0, 14, 56, 84, and 112, as shown in FIG. 15A. As shown in FIG. 15B, prior to treatment, patients experienced an average of 5.23 incontinence episodes per day. At day 14, the average daily incontinence episodes were reduced to 2.9, a 44% decrease from baseline. At day 56, the average daily incontinence episodes were reduced to 3.0, a 43% decrease from baseline. At day 84, the average daily incontinence episodes were reduced to 2.3, a 56% decrease from baseline. This indicates that extended local delivery of trospium to the bladder is effective for treating overactive bladder.

The invention claimed is:

1. A method of treating idiopathic overactive bladder in an individual that has received a prior oral therapy, comprising
    i) a first phase comprising continuously administering an effective amount of trospium to the bladder of the individual for at least about 42 days, and
    ii) a maintenance phase comprising continuously administering an effective amount of trospium to the bladder of the individual for at least about 42 days,
    wherein the maintenance phase is initiated upon symptom reoccurrence following the first phase.

2. The method of claim 1, wherein trospium is administered to the bladder of the individual for at least about 84 days during the first phase.

3. The method of claim 1, wherein the individual did not respond or was refractory to the prior oral therapy.

4. The method of claim 1, wherein trospium is administered to the bladder using an intravesical device.

5. The method of claim 4, wherein the intravesical device comprises about 850 mg of trospium.

6. The method of claim 4, wherein about 10 mg/day of trospium is released from the intravesical device over a 42 day period during the first phase or the maintenance phase.

7. The method of claim 1, wherein the individual experiences symptom relief for at least about 7 days after trospium administration is completed.

8. The method of claim 7, wherein the individual experiences symptom relief for at least about 6 weeks after trospium administration is completed.

9. The method of claim 2, wherein the individual experiences symptom relief for at least about 7 days after trospium administration is completed.

10. The method of claim 9, wherein the individual experiences symptom relief for at least about 4 weeks after trospium administration is completed.

11. The method of claim 7, wherein the symptom relief comprises a relief of urgency, frequency, or incontinence.

12. The method of claim 9, wherein the symptom relief comprises a relief of urgency, frequency, or incontinence.

13. The method of claim 1, wherein the concentration of trospium in the plasma of the individual is less than 2 ng/ml during administration of trospium.

14. The method of claim 1, wherein the concentration of trospium in the urine is between about 0.1 and about 100 μg/ml during administration of trospium.

15. The method of claim 14, wherein the concentration of trospium in the urine is between about 2 and about 8 μg/ml during administration of trospium.

16. The method of claim 1, wherein the individual has an improved quality of life score upon treatment with trospium.

17. The method of claim 1, wherein the individual has a reduced urinary bother score upon treatment with trospium.

18. The method of claim 1, wherein trospium is administered to the bladder of the individual for at least about 84 days during the maintenance phase.

19. The method of claim 1, wherein the maintenance phase is initiated at least about 1 week after the completion of the first phase.

20. The method of claim 1, wherein the maintenance phase is initiated about 3 months after the completion of the first phase.

* * * * *